US012810854B2

(12) United States Patent
Ganmukhi et al.

(10) Patent No.: US 12,810,854 B2
(45) Date of Patent: Nov. 24, 2026

(54) SYSTEMS AND METHODS FOR VOICE ASSISTANT FOR ELECTRONIC HEALTH RECORDS

(71) Applicant: Bola Technologies, Inc., Laguna Beach, CA (US)

(72) Inventors: Rushi M. Ganmukhi, Laguna Beach, CA (US); Paritosh Katyal, Boston, MA (US); Augusto Monteiro Nobre Amanco, Centro (BR); Christine Long, Norwood, MA (US); Firshta Shefa, Denver, CO (US); Muthouazhagi Dhanapal, Centreville, VA (US); Tarangini Sarathy, Boston, MA (US)

(73) Assignee: Bola Technologies, Inc.

( * ) Notice: Subject to any disclaimer, the term of this patent is extended or adjusted under 35 U.S.C. 154(b) by 180 days.

(21) Appl. No.: 18/422,491

(22) Filed: Jan. 25, 2024

(65) Prior Publication Data

US 2024/0257807 A1 Aug. 1, 2024

Related U.S. Application Data

(60) Provisional application No. 63/441,240, filed on Jan. 26, 2023.

(51) Int. Cl.
*G10L 15/22* (2006.01)
*G16H 10/60* (2018.01)

(52) U.S. Cl.
CPC ............ *G10L 15/22* (2013.01); *G16H 10/60* (2018.01)

(58) Field of Classification Search
USPC ......................... 704/246, 247, 251, 252, 275
See application file for complete search history.

(56) References Cited

U.S. PATENT DOCUMENTS

| | | | | |
|---|---|---|---|---|
| 10,729,502 B1 * | 8/2020 | Wolf | ...................... | G16H 50/70 |
| 2018/0197548 A1 * | 7/2018 | Palakodety | ............. | G10L 17/06 |
| 2022/0115134 A1 * | 4/2022 | Strader | .................. | G10L 15/08 |
| 2023/0113548 A1 * | 4/2023 | D'Agostino | ........... | G16H 15/00 705/3 |
| 2023/0352127 A1 * | 11/2023 | Sivan | .................... | G06F 40/279 |

* cited by examiner

*Primary Examiner* — Leonard Saint-Cyr
(74) *Attorney, Agent, or Firm* — Foley & Lardner LLP

(57) ABSTRACT

An electronic record voice assistant system can include one or more processors that receive audio data, apply a machine learning model to the audio data to generate speech data including at least one value, determine a state of an electronic record, and update one or more fields of the electronic record using the state and the at least one value.

20 Claims, 8 Drawing Sheets

SYSTEMS AND METHODS FOR VOICE ASSISTANT FOR ELECTRONIC HEALTH RECORDS

CROSS-REFERENCE TO RELATED APPLICATIONS

The present application claims the benefit of and priority to U.S. Provisional Application No. 63/441,240, filed Jan. 26, 2023, the disclosure of which is incorporated herein by reference in its entirety.

BACKGROUND

The present disclosure relates generally to the field of electronic record technology, and more particularly to systems and methods for voice assistants for electronic health records.

Electronic health record technology, including but not limited to practice management software, practice management systems (PMs), electronic health records (EHRs), electronic medical records (EMRs), CardioVascular Information Systems (CVIS), Patient Charting Systems, Procedure Documentation Systems, and electronic dental records, can be used to maintain information regarding patients for subsequent retrieval and analysis. The information may be provided through various user interfaces in order to be stored in the electronic health record.

SUMMARY

At least one aspect relates to a system. The system can include one or more processors that receive audio data, apply a machine learning model to the audio data to generate speech data including at least one value, determine a state of an electronic record, and update one or more fields of the electronic record using the state and the at least one value. At least one command can be determined (e.g., inferred) based on the speech data or the at least one value, and used to update the one or more fields.

At least one aspect relates to a method. The method can include receiving an audio input indicating a command, pre-processing the audio input to generate audio data, generating text data by applying a speech model to the audio data, generating at least one value from the text data, determining a state of an electronic record, and updating the electronic record using the at least one value based on the state.

At least one aspect relates to a method of using voice commands to update electronic dental records. The method can include receiving, by one or more processors, audio data; applying, by the one or more processors, a speech model to the audio data to generate speech data including at least one value; determining, by the one or more processors, a state of a periodontal chart data object, the periodontal chart data object including a plurality of fields, each field associated with a tooth or gingiva of a subject and at least one feature of the tooth, the state corresponding to a particular field of the plurality of fields; determining, by the one or more processors, a command based on at least one of the speech data or the at least one value; and assigning, by the one or more processors, the at least one value to the at least one feature of the tooth based on the command and the state.

At least one aspect relates to a method of integrating an electronic voice assistant with electronic records. The method can include receiving, by one or more processors, audio data; applying, by the one or more processors, a speech model to the audio data to generate speech data including at least one value; determining, by the one or more processors, a state of an electronic record, the electronic record including a plurality of fields; determining, by the one or more processors, a command based on at least one of the speech data or the at least one value; identifying, by the one or more processors, a particular field of the plurality of fields based on the state; and assigning, by the one or more processors, the at least one value to the particular field based on the command and the state.

At least one aspect relates to a method. The method can include determining, by one or more processors, by processing an electronic record associated with a subject, a state of at least one tooth of the subject; determining, by the one or more processors based at least on the state, a procedure to be applied to the at least one tooth; receiving, by the one or more processors, audio data during the procedure; determining, by the one or more processors by applying the audio data to a speech model, speech data representative of the audio data based at least on the state; and assigning, by the one or more processors, the speech data to the electronic record based at least on the state.

At least one aspect relates to a system. The system can include one or more processors configured to determine, by processing an electronic record associated with a subject, a state of at least one tooth of the subject; determine, based at least on the state, a procedure to be applied to the at least one tooth; receive audio data during the procedure; determine, by applying the audio data to a speech model, speech data representative of the audio data based at least on the state; and assign the speech data to the electronic record based at least on the state.

At least one aspect relates to a method. The method can include determining, by one or more processors, by processing an electronic record associated with a subject, a gastrointestinal state of the subject; determining, by the one or more processors based at least on the gastrointestinal state of the subject, a gastrointestinal procedure to be performed on the subject; receiving, by the one or more processors, audio data during the gastrointestinal procedure; determining, by the one or more processors by applying the audio data to a speech model, speech data representative of the audio data based at least on the gastrointestinal state; and assigning, by the one or more processors, the speech data to the electronic record based at least on the gastrointestinal state.

At least one aspect relates to a system. The system can include one or more processors configured to determine, by processing an electronic record associated with the subject, a gastrointestinal state of the subject; determine, based at least on the gastrointestinal state of the subject, a gastrointestinal procedure to be performed on the subject; receive audio data during the gastrointestinal procedure; determine, by applying the audio data to a speech model, speech data representative of the audio data based at least on the gastrointestinal state; and assign the speech data to the electronic record based at least on the gastrointestinal state.

At least one aspect relates to a method. The method can include determining, by one or more processors, based on a subject data record, a state of a subject for a cardiology procedure; receiving, by one or more processors, audio data during the cardiology procedure; determining, by the one or more processors by applying the audio data and the state to a speech model, speech data representative of the audio data, the speech model configured based on training data including training audio data, speech data corresponding to the training audio data, and at least one of an identifier of a procedure or a training state of a training subject; and assigning the speech data to at least one field of the subject data record.

At least one aspect relates to a system. The system can include one or more processors configured to determine, based on a subject data record, a state of a subject for a cardiology procedure; receive audio data during the cardiology procedure; determine, by applying the audio data and the state to a speech model, speech data representative of the audio data, the speech model configured based on training data including training audio data, speech data corresponding to the training audio data, and at least one of an identifier of a procedure or a training state of a training subject; and assign the speech data to at least one field of the subject data record.

At least one aspect relates to a method. The method can include determining, by one or more processors, based on a subject data record of the subject, a state of the subject; determining, by the one or more processors, based on at least one of the subject data record or audio data, a procedure to be performed on the subject; retrieving, by the one or more processors, at least one speech model corresponding to the procedure, the at least one speech model configured using training data comprising one or more training audio data representative of the procedure and training speech data corresponding to the training audio data; detecting, by the one or more processors, during the procedure, procedure audio data; determining, by the one or more processors, speech data corresponding to the procedure audio data by applying the procedure audio data as input to the at least one speech model; and assigning, by the one or more processors, based on at least one of the state or the procedure, the speech data to one or more fields of the subject data record.

At least one aspect relates to a system. The system can include one or more processors configured to determine, based on a subject data record of the subject, a state of the subject; determine, based on at least one of the subject data record or audio data, a procedure to be performed on the subject; retrieve at least one speech model corresponding to the procedure, the at least one speech model configured using training data comprising one or more training audio data representative of the procedure and training speech data corresponding to the training audio data; detect, during the procedure, procedure audio data; determine speech data corresponding to the procedure audio data by applying the procedure audio data as input to the at least one speech model; and assign, based on at least one of the state or the procedure, the speech data to one or more fields of the subject data record.

At least one aspect relates to a method. The method can include detecting, by one or more processors, a domain of a procedure being performed on a subject. The method can include receiving, by the one or more processors, audio data during the procedure. The method can include detecting, by the one or more processors, a state of an electronic record associated with the subject. The method can include applying, by the one or more processors, the domain and the audio data as input to at least one machine learning model to cause the at least one machine learning model to generate speech data representative of the audio data that comprises (1) a command for navigation of the electronic record and (2) a value for entry in the electronic record. The method can include selecting, by the one or more processors, a field of the electronic record based at least on the state and the command. The method can include assigning, by the one or more processors, the value to the field.

At least one aspect relates to a system. The system can include one or more processors to detect a domain of a procedure being performed on a subject. The one or more processors can receive audio data during the procedure. The one or more processors can detect a state of an electronic record associated with the subject. The one or more processors can apply the domain and the audio data as input to at least one machine learning model to cause the at least one machine learning model to generate speech data representative of the audio data that comprises (1) a command for navigation of the electronic record and (2) a value for entry in the electronic record. The one or more processors can select a field of the electronic record based at least on the state and the command. The one or more processors can assign the value to the field.

These and other aspects and implementations are discussed in detail below. The foregoing information and the following detailed description include illustrative examples of various aspects and implementations, and provide an overview or framework for understanding the nature and character of the claimed aspects and implementations. The drawings provide illustration and a further understanding of the various aspects and implementations, and are incorporated in and constitute a part of this specification.

BRIEF DESCRIPTION OF THE DRAWINGS

The accompanying drawings are not intended to be drawn to scale. Like reference numbers and designations in the various drawings indicate like elements. For purposes of clarity, not every component can be labeled in every drawing. In the drawings.

DETAILED DESCRIPTION

Figure 1:
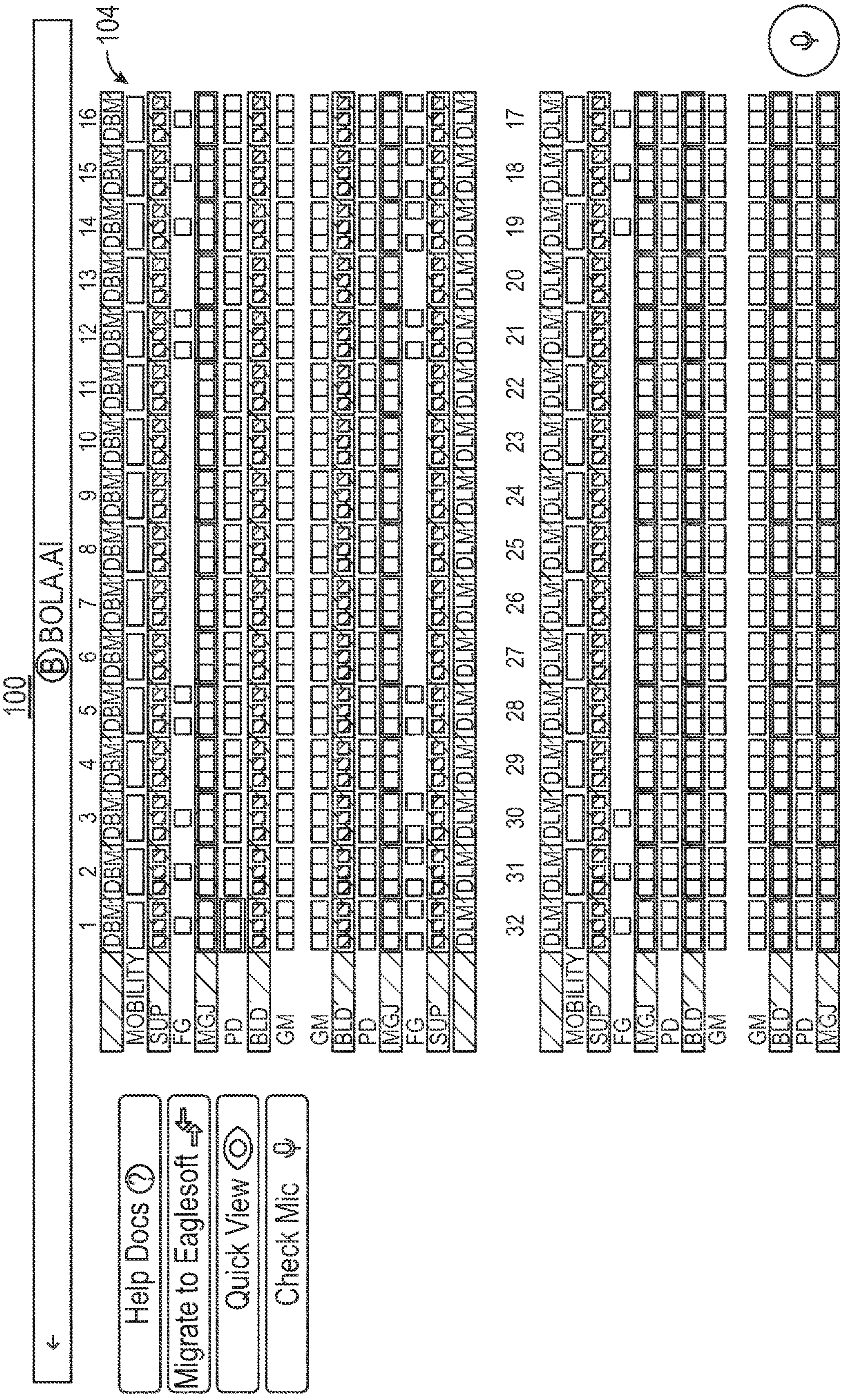
FIG. 1 depicts an example of an electronic health record.

Electronic health record technologies, such as for medical and dental databases (e.g., practice management software, electronic dental records, PMs, EMRs, EHRs, CardioVascular Information Systems (CVIS), Patient Charting Systems, Procedure Documentation Systems), can be updated using information received through various user interfaces. For example, a client device can operate an application or a browser-based interface that can receive subject data regarding a subject or patient. This can include, for example, dental records and databases that include or operate with electronic medical records, electronic dental records, practice management systems, treatment planning, and patient charting software. Similarly, medical procedures and dental procedures, such as endoscopic, gastrointestinal, cardiological, and other procedures that involve detecting information regarding the subject, applying treatment to the subject, or various combinations thereof, can be performed together with subject data acquisition regarding specific aspects of the procedures. Various such records and databases can also include or operate with customer relationship management (CRM) and enterprise resource planning (ERP) technologies.

Electronic tools, such as voice assistants, can receive the subject data in order to provide the subject data to the database. However, it can be difficult to accurately detect the subject data from speech provide to the voice assistant. For example, during some procedures, there may be conversational speech amongst the participants in the procedure (e.g., medical professionals, dental professionals, subjects, etc.) that may not necessarily be pertinent for recording to subject data records in all instances. As such, there may be a relatively high proportion of noise that voice assistant and/or speech processing components may detect during procedures (e.g., both ambient noise from machinery in the room in which the procedure is taking place as well as speech that may not necessarily be pertinent to a particular aspect of a data record). For example, it can be difficult for speech detection to be performed with sufficient accuracy/precision (e.g., metrics related to correctly determining speech and/or specific speech elements, commands, and/or fields to assign speech to in the data record, from input audio) and recall (e.g., correctly identifying speech for assigning to the data record vs. for not assigning to the data record where not pertinent).

It can also be difficult for a computer program to automatically and accurately navigate the user interface that receives the subject data. Errors in both speech detection and user interface navigation can compound each other, and such errors can reduce the quality of the user experience during real-time data recording and/or not be detected during post-procedure data recording.

Systems and methods in accordance with the present disclosure can enable a voice assistant to accurately process received audio in order to detect speech, including subject data and commands associated with the subject data, improve the speech models used for the speech detection, and accurately navigate the user interface to assign subject data to appropriate fields in the user database. This can enable electronic records to be accurately updated without requiring a user to take actions in both a sterile field (e.g., while in contact with a subject) and a non-sterile field (e.g., while in contact with a computing device). Systems and methods as described herein can enable more accurate and timely assignment of data (through user interfaces) to appropriate fields in databases including but not limited to PM, EHR, EMR, electronic dental record, CRM, and ERP databases. For example, a state of an electronic data record to which data is to be assigned can be monitored and validated based on the data being provided for assignment (e.g., with or without user input that confirms the state information).

As described further herein, systems and methods in accordance with the present disclosure can accurately provide inputs to and read information from a user interface of an application (e.g., front-end application) connected with the database (e.g., backend database), facilitating the ability to update the database and monitor state information without requiring a user to manually interact with the client device that presents the user interface or break a sterile field. For example, the system can use computer vision or other image processing algorithms, HTML processing, or various combinations thereof, to detect state, value, and configuration information of the user interface (e.g., read text data presented on the user interface). The system can use input entry processes such as robotic process automation (e.g., mimicking of keystrokes and mouse clicks) to provide inputs to the database through the user interface and the application. The system can optimize keypress combinations to move between sections of restorative and periodontal charts to provide an end-to-end experience for the dental health practitioner. The system can detect commands from speech data. For example, the system can determine, from speech data, a command such as "amalgam filling on tooth number 5 occlusal, class IV." As such, the application, responsive to receiving the inputs from the system, can update the database and the user interface to present information corresponding to the command. The system can standardize documentation of findings in the EHR using preset templates. The system can accurately detect subject data despite large amounts of noise.

Systems and methods in accordance with the present disclosure can enable a voice assistant to accurately process received audio in order to detect speech, including subject data and commands associated with the subject data, improve the speech models used for the speech detection, and accurately navigate the user interface to assign subject data to appropriate fields in the user database. This can enable electronic records to be accurately updated without requiring a user to take action in both a sterile field and a non-sterile field. Systems and methods as described herein can enable more accurate and timely assignment of data (through the user interfaces) to appropriate fields in databases including but not limited to PM, EHR, EMR, electronic gastrointestinal, CRM, and ERP databases. For example, a state of an electronic record to which data is assigned can be monitored and validated based on the data being provided for assignment (e.g., with or without user input that confirms state information).

As described further herein, systems and methods in accordance with the present disclosure can accurately provide inputs to and read information from a user interface of an application (e.g., front-end application) connected with the database (e.g., backend database), facilitating the ability to update the database and monitor state information without requiring a user to manually interact with the client device that presents the user interface or break a sterile field. For example, the system can use computer vision or other image processing algorithms to detect state, value, and configuration information of the user interface (e.g., read text data presented on the user interface). The system can use input entry processes such as robotic process automation (e.g., mimicking of keystrokes and mouse clicks) to provide inputs to the database through the user interface and the application. The system can optimize keypress combinations to provide time stamp data, label abnormal findings, and create labels to identify biopsies of abnormal findings to provide an end-to-end experience for the dental health practitioner. The system can detect commands from speech data. For example, the system can determine, from speech data, a command such as "found polyp, sigmoid colon, 100 mm, semi-sessile, cold snare, not resected." As such, the application, responsive to receiving the inputs from the system, can update the database and the user interface to present information corresponding to the command. The system can standardize documentation of findings in the EHR using preset templates. The system can accurately detect subject data despite large amounts of noise. Various such systems and methods can allow for seamless integration with EHRs, including EHRs having cloud or desktop-based interfaces.

The system can use speech models (e.g., machine learning models, neural networks, natural language processing models, natural language generation models, or various combinations thereof) to more effectively detect speech and assign the detected speech to specific fields in data records (including to freeform fields), including in the context of procedures with relatively high noise audio. For example, the speech models can be trained or otherwise configured using training data that includes audio which may be implicitly (e.g., where the training data includes example data records having speech data assigned to the data records) or explicitly annotated (e.g., by an annotation indicating that the speech is to be assigned) to indicate whether speech data corresponding to the audio is of a class or category for assignment to data records. The speech models can be configured to use a state associated with at least one of the subject or the data record to determine speech from audio data, such as by performing training conditioned on state information (e.g., condition-free guidance). For example, the state may indicate at least one of a particular anatomical feature of the subject or a characteristic of the anatomical feature, and the speech model can determine the speech data from the audio data according to the state, such as to be configured so that confidence scores and/or probability scores associated with candidate speech outputs from the models can be conditioned on or otherwise modified based on the state. This can enable the speech models to more effectively and accurate detect relevant speech for assignment to data records from other speech.

FIG. 1 depicts an example of a representation of an electronic record 100. The electronic record 100 can be a record object of a database, including but not limited to a database for practice management software, PMs, EHRs, EMRs, electronic dental records, CRM, and ERP technologies. The electronic record 100 can include a plurality of fields to which data can be assigned. Each electronic record 100 can be associated with a subject, such as a patient (including but not limited to an event associated with the subject, such as a treatment, procedure, or other interaction, such as a meeting or call). The electronic record 100 can include data from multiple points in time (e.g., to maintain longitudinal data regarding the subject). For example, the electronic record 100 can include data recorded from multiple events in which a subject undergoes a procedure or other medical or dental interaction. The electronic record 100 can include or receive at least one of structured data (e.g., data expected to be assigned to particular respective fields) or unstructured data (e.g., data corresponding to streams of text that can be assigned to various fields).

The electronic record 100 can be presented using a client device, and can receive subject data using a user interface of the client device. The client device can maintain at least a portion of the electronic record 100. The electronic record 100 can be maintained by a server device remote from the client device, and the client device can communicate the subject data to the server device to update the electronic record 100. The electronic record 100 can be maintained by an application native to one or more client devices (e.g., without the use of a server, such as by implementing the electronic record 100 and the user interface on a single client device, or implementing the electronic record 100 on a first client device (e.g., desktop computer) and the user interface on a second client device (e.g., portable electronic device), among other configurations).

As depicted in FIG. 1, the electronic record 100 can include a periodontal chart data object 104. The periodontal chart data object 104 can include structured data, such as fields associated with teeth of the subject and features of the teeth. The periodontal chart data object 104 can have values assigned to the fields responsive to receiving the subject data. For example, the periodontal chart object 104 can be used for a periodontal charting procedure in which a user, such as a dental hygienist, measures health of gums (e.g., using a probe to measure gum depths and other various of each tooth, which may include taking around 400 measurements in ten minutes). For example, periodontal values such as pocket depths, bleeding points, gingival margin/recession, suppuration, mucogingival junction, furcation, and mobility, among others, can be entered. Values can be assigned to a current tooth (e.g., bleeding on all sides, bleeding on mesial side, gingival margin with 323), other teeth (e.g., bleeding on tooth 3 all, gingival margin tooth number 10 with 323), multiple teeth (bleeding sextant one, repeat 010 on tooth number 10 to tooth number 16), and various combinations thereof. Commands to navigate the electronic record 100 can be provided, such as jump, go to, move, skip, go back, or undo.

Figure 2:
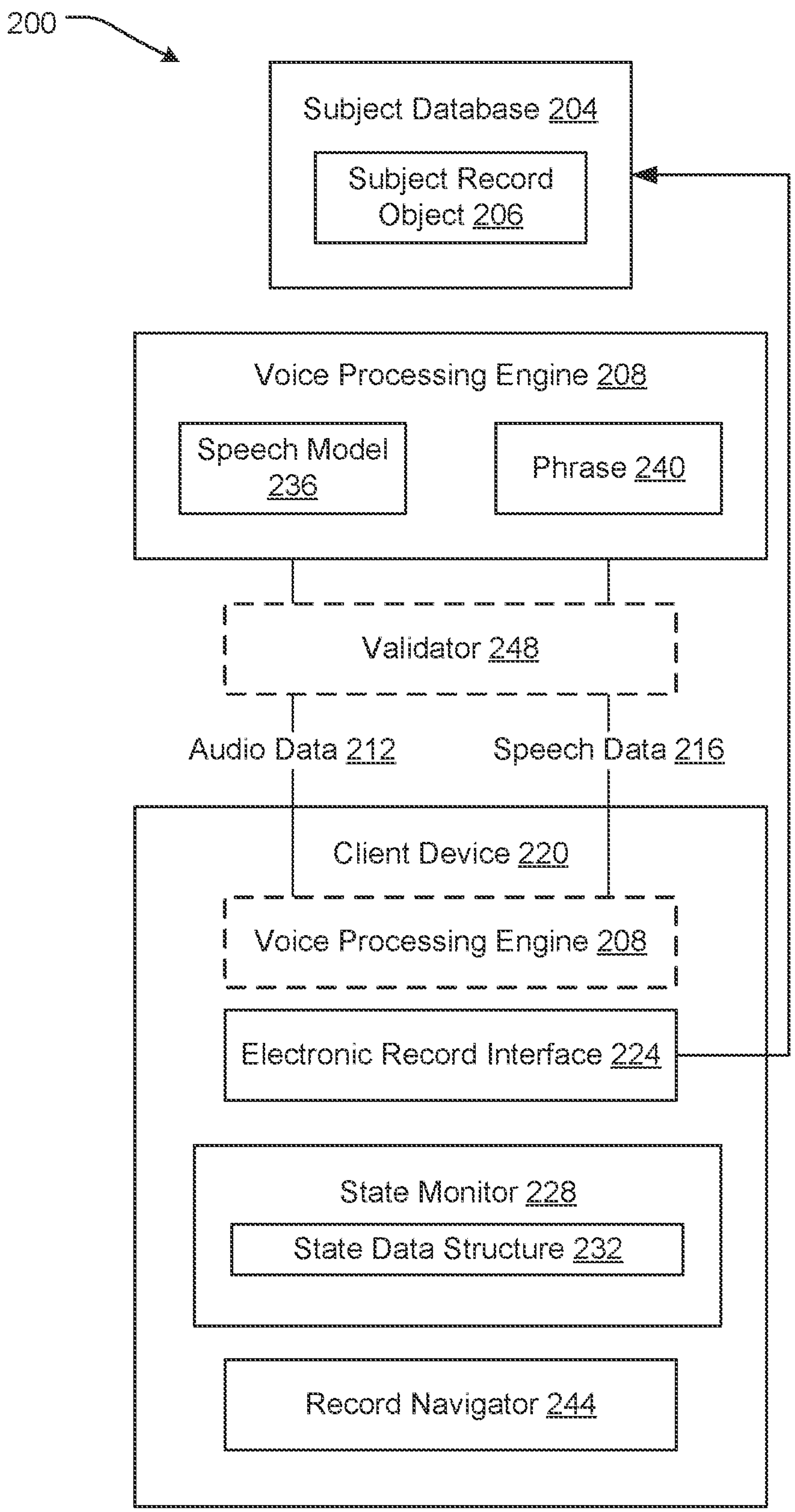
FIG. 2 depicts a block diagram of an example of an electronic record voice assistant system.

FIG. 2 depicts an example of an electronic record voice assistant system 200 (hereinafter referred to as system 200). The system 200 and components thereof can be implemented using various features of the computing environment 1000 described with reference to FIGS. 10A-10B. Various components of the system 200 can be implemented using one or more computing devices; for example, the subject database 204 can be implemented using one or more first servers, and the voice processing engine 208 can be implemented using one or more second servers (or by a native application operating on a desktop client that implements a native application for the electronic record). Various aspects of the system can be implemented as a web browser or extension (e.g., if the electronic record is accessed through a web-based interface) or as a desktop application (e.g., if the software associated with the electronic record is a native application). The system 200 can be fully integrated into the electronic record 100 (e.g., as a single application in which the system 200 includes the electronic record 100 and/or a database that includes the electronic record 100). The system 200 can be used to detect states of and detect speech relating to various teeth and/or gingiva (e.g., gums, soft tissue) of subjects. For example, the system 200 can be used to facilitate existing restorations or procedures as well as new restorations or procedures or conditions (e.g., during treatment planning or after completion).

The system 200 can use voice commands to control web-based and native electronic health records, including by identifying user inputs (e.g., commands) programmatically and manipulating interfaces that present the electronic health records based on the commands. The system 200 can be used for various medical and dental electronic records, such as for periodontal charting, tooth/restorative charting, electronic health record navigation, treatment planning, transcribing clinical notes from speech data, and messaging between operatories. The system 200 can be used to detect and implement the various commands and record value updates described with reference to the electronic record 100 of FIG. 1. The system 200 can be used to retrieve and assign structured data from sales or support calls or meetings for CRM databases (e.g., from a recording of a call or meeting from which audio data can be retrieved). This can include, for example, implementing the system 200 to allow a sales person to seamlessly enter data into the CRM database while on a sales call with a prospective customer. The system 200 can be used to retrieve and assign structured data such as notes into an ERP database (e.g., notes dictated by a mechanic).

The system 200 can include a subject database 204. The subject database 204 can store and maintain record objects 206 for various subjects. The record objects 206 can include the electronic record 100 and features thereof described with reference to FIG. 1. The record objects 206 can include subject profile data, such as name, age or date of birth, height, weight, sex, and medical history information.

The system 200 can include a voice processing engine 208. Briefly, the voice processing engine 208 can receive audio data 212 and process the audio data to detect speech data 216 from the audio data 212. The audio data 212 can be retrieved in real-time or near real-time, or can be stored and retrieved at a subsequent time for processing (e.g., for batch processing, including batch processing of CRM or ERP data). As depicted in FIG. 2, a client device 220 can operate an electronic record interface 224. The electronic record interface 224 can be used to implement the electronic record 100 as described with reference to FIG. 1. The client device 220 can receive user input to be used to update the electronic record 100. While the user input may be provided through user input devices such as a keyboard and mouse, this manner of providing user input may be inefficient. As such, the client device 220 can receive an audio input (e.g., via a microphone) and provide the audio input as audio data 212 to the voice processing engine 208. The electronic record interface 224 can perform computer vision on the images displayed by the client device 220 (e.g., images displayed of the electronic record 100) to detect text and other information of the images (e.g., using various computer vision models or functions that can perform text recognition, including by matching image data with templates of text information), including to retrieve information from the electronic record 100 (this can, for example, enable the system 200 to identify the subject of the electronic record 100 to validate that the subject corresponds to the subject regarding which feedback is being received or output an error if the subject of the electronic record 100 does not correspond to the subject regarding which feedback is being received). The electronic record interface 224 can perform robotic process automation (RPA) to provide at least one of a keystroke and mouse movement to the client device 220 to input data into the electronic record 100.

As depicted in FIG. 2, at least a portion of the voice processing engine 208 can be implemented by the client device 220 (e.g., in addition to a server device remote from and communicatively coupled with the client device 220). For example, the voice processing engine 208 can be implemented by a front end application, such as a desktop application, plugin application, or mobile application, that can perform at least some processing of the audio data 212 prior to transmitting (e.g., streaming) the processed audio data 212 to another portion of the voice processing engine 208 implemented using the remote server device (e.g., a cloud-based server). The front end application can perform various processing of the audio data 212, such as filtering or compressing. The front end application can be triggered to record and perform at least a portion of the speech processing by an audio command (e.g., wake word to activate a microphone of the client device 220 to detect audio representing speech data), and the client device 220 can perform a remainder of the speech processing or transmit the partially processed speech data to the server. As such, part or all of the speech processing performed by the voice processing engine 208 can occur on the client device 220 (e.g., operating the system 200 on the edge, such as operating the voice processing engine 208 and speech model 236 on the edge), and such allocation of speech processing can be determined or modified based on security or processing capacity factors.

The system 200 can include a state monitor 228. The state monitor 228 can be implemented by the client device 220, such as by the front end application that implements at least a portion of the voice processing engine 208. The state monitor 228 can include and maintain a state data structure 232 of the electronic record interface 224. The state data structure 232 can be a data structure that indicates a state (e.g., current location) in the electronic record 100 implemented by the electronic record interface 224.

For example, the state data structure 232 can include fields indicating values of the state such as a tooth and a side of the tooth. For example, the state data structure 232 can include fields corresponding to the fields of the periodontal chart data object 104 depicted in FIG. 1, such as tooth field (e.g., the tooth field can have a value of '2') and a side field (e.g., the side field can have a value of 'buccal').

The voice processing engine 208 can receive the audio data 212 (e.g., the processed audio data 212) and generate the speech data 216 responsive to receiving the audio data 212. The voice processing engine 208 can apply various language processing systems, logic, or models to the audio data 212 to generate the speech data 216.

The voice processing engine 208 can include at least one speech model 236. The speech model 236 can be a machine learning model trained to generate the speech data 216 responsive to the audio data 212. For example, the speech model 236 can be trained using supervised learning, such as by providing, as input to the speech model 236, audio data, causing the speech model 236 to generate candidate outputs (e.g., candidate speech), comparing the candidate outputs to known values of the speech represented by the audio data, and adjusting the speech model 236 (e.g., adjusting various weights or biases of the speech model 236) responsive to the comparison to satisfy a convergence condition, such as a predetermined number of iterations or a threshold difference between the candidate outputs and the known values.

For example, the speech model 236 can be trained using audio data representing structured information and commands, such as "jump to tooth number 3." The speech model 236 can include various machine learning models, such as a neural network trained using training data including audio and vocabulary for a particular domain (e.g., dental domain). The voice processing engine 208 can provide the audio data 212 to the at least one speech model 236 to cause the at least one speech model 236 to generate at least one phrase 240. The speech model 236 can assign a confidence score to each phrase 240; the confidence score can indicate an expectation of the accuracy of the phrase 240. The voice processing engine 208 can output the speech data 216 based on at least one the phrase 240; for example, if the speech model 236 outputs a plurality of phrases 240, the voice processing engine 208 can select one or more phrases 240, such as by comparing the confidence scores of the phrases 240 to a confidence threshold and selecting phrase(s) 240 that meet or exceed the threshold, selecting a phrase 240 having a highest confidence score, or various combinations thereof.

The voice processing engine 208 can include an intent engine (e.g., natural language processor) that can detect intents (e.g., commands and values) from the speech data 216 and/or the phrases 240. In some implementations, the voice processing engine 208 determines the at least one command from the at least one value of the at least one phrase 240. For example, particular values, numbers of values, or orderings of values may be associated with particular commands in order to determine the command (e.g., rather than determining the command from the speech data 216 itself). The voice processing engine 208 can process speech data 216 that may or may not include pauses between words, phrases, or other components of the speech data 216. For example, the speech data 216 may represent a pauseless multicommand input, in which multiple commands and/or values or represented without pauses between the commands and/or values.

The voice processing engine 208 can process speech data 216 nonsequentially, in portions (e.g., streams, chunks), or various other such formats, which can enable the overall processing of the speech data 216 to be more rapid and accurate. For example, the voice processing engine 208 can return a first phrase 240 from the speech data 216 (and assign the first phrase 240 to a corresponding field of the electronic record 100) and continue processing the speech data 216 to detect one or more second phrases 240 (e.g., subsequent to assigning the first phrase 240 to the corresponding field). For example, responsive to determining an intent of the speech data 216, the voice processing engine 208 can identify the first phrase 240 and continue to process the speech data 216 to identify the one or more second phrases 240. For example, responsive to identifying a sequence of three numbers from the speech data 216, the voice processing engine 208 can assign the three numbers to a field corresponding to the three numbers, even as additional speech data 216 (whether received before or after the three numbers) is being processed.

In some implementations, the voice processing engine 208 uses the state data structure 232 and the at least one phrase 240 to generate the speech data 216. For example, the voice processing engine 208 can apply various rules, policies, heuristics, models, or logic to the at least one phrase 240 based on the state data structure 232 to generate the speech data 216, such as to modify or update the confidence scores of the phrases 240. For example, the state data structure 232 can be used to determine an expectation of what the phrase 240 should be, as the state of the electronic record 100 represented by the state data structure 232 can indicate a likelihood of what subject data and commands are represented by the audio data 212. For example, if the state data structure 232 indicates that the state of the electronic record 100 is at tooth number 3, the voice processing engine 208 can assign a higher confidence to a particular phrase 240 that indicates subject data regarding tooth number 4 rather than tooth number 12 (e.g., based on rules or logic indicative of proximity or other spatial relationships between teeth). The state data structure 232 can be used to determine a command based on values represented by the speech data 216.

The system 200 can use the speech data 216 to update the electronic record 100 using the electronic record interface 224. For example, the system 200 can provide the speech data 216 to the client device 220 (e.g., to the front end application implemented by the client device 220) to update the subject record object 206 corresponding to the subject using the electronic record interface 224.

In some implementations, the system 200 uses feedback regarding the speech data 216 to update the at least one speech model 236. The system 200 can receive feedback such as whether the speech data 216 satisfies an upper confidence threshold (e.g., indicating that the detected speech values are definitely right) or does not satisfy a lower confidence threshold (e.g., indicating that the detected speech values are definitely wrong), such as based on user input indicative of the feedback, or based on information received from the validator 248 described further herein.

Referring further to FIG. 2, the at least one speech model 236 can process the speech data 216 to detect a target function for the speech data 216, such as an action to be performed (e.g., command) represented by the speech data 216. The at least one speech model 236 can detect the target function by applying the speech data 216 (or a portion thereof) as input to one or more rules, lookup tables, models, or algorithms that map speech data 216 with target functions. The target functions can be data input commands for use with the client device 220, such as JSON and/or HTML commands for navigation and data entry on the electronic record 100 by the electronic record interface 224. In some implementations, responsive to mapping the speech data 216 with the target function, the at least one speech model 236 can generate an output in a format for reception by the client device 220, such as in JSON format. The use of the target function mapping can facilitate more accurate generation of commands for navigation and data entry, which can mitigate or negate issues with latency in operation of the electronic record interface 224 and/or reduce the number of instances of audio data 212 processing required to assign speech data 216 to the electronic record 100.

The at least one speech model 236 can include one or more machine learning models, including but not limited to one or more neural networks. The one or more machine learning models can include one or more deep learning neural networks. The one or more machine learning models can include one or more transformers, generative pre-trained models (GPTs), recurrent neural networks (RNNs), convolutional neural networks (CNNs), long short-term memory (LSTM) models, large language models (LLMs), sequence models, autoregressive models, encoder models, or various combinations thereof. The use of one or more such neural network-based machine learning architectures can facilitate speech detection that is more accurate, lower latency, and/or has lower computational and network demands.

One or more neural networks of the at least one speech model 236 can be trained or pre-trained on domain-independent and/or domain-specific data (e.g. and without limitation, data corresponding to domains such as dental, periodontal, restorative, surgical, cardiological, GI, or CRM processes, or various other applications). The at least one speech model 236 can include an end-to-end model to perform operations such as (1) determine an understanding (e.g., detect at least one of the domain or the target function) of the domain and phrase(s) of the audio data, including by detecting a semantic feature of the audio data corresponding to the domain and phrases(s) and/or represented by the speech detected by the at least one speech model 236; (2) transcribing the audio data into text of speech data; and/or (3) detecting one or more commands and corresponding one or more values for the one or more commands, which can including distinguishing a first command from a second command in a phrase or other unit of audio data input; or the at least one speech model 236 can include a plurality of speech models 236 to perform one or more such operations. The structuring of the at least one speech model 236 to perform such functions can allow for the at least one speech model 236 to detect key aspects of speech data 216 (e.g., boundaries, target functions, commands) to facilitate more accurate speech data 216 detection.

The system 200 can include or be coupled with a training database that includes training data for configuration of the at least one speech model 236. The training data can include any one or more of text, audio, speech, image, and/or video data, which can be mapped with one another to represent example inputs and outputs for the at least one speech model 236. The training data can include a plurality of training data elements, such as where each training data element includes an item of audio data and a corresponding item of speech data (e.g., text corresponding to the audio data). In some implementations, a given training data element can be assigned an indicator of a context (e.g., domain) for the audio data, such as to indicate that the audio data corresponds to dental, procedural, GI, cardiovascular, surgical, or CRM data, for example and without limitation. The training data elements can include data from example speech recordings, such as where a speaker is presented a phrase to speak (corresponding to the speech data of the training data element), and the phrase is recorded as the audio data. The training data elements can include real-world data, such as recordings of audio data (which may have corresponding manual transcriptions, or automated transcriptions from other systems, for the speech data). The training data can include synthetic data, such as data generated by inputting text into a text-to-speech model.

In some implementations, one or more training data elements include or are modified by an audio modification. The audio modification can include one or more of noise, background audio, frequency changes, amplitude changes, speech changes, or various combinations thereof. In some implementations, modifications such as noise and/or background audio are included from real-world settings for the domain for the at least one speech model 236, which can facilitate training the at least one speech model 236 to perform more effectively in real-world situations in which the at least one speech model 236 is to be deployed. This can include, for example, training the at least one speech model 236 using a first subset of training data that include audio modifications, and a second subset of training data that does not include audio modifications. As such, at inference time, the at least one speech model 236 can more effectively filter out noise, background audio or speech, or other extraneous information, which can result in more accurate determination of speech data 216.

The at least one speech model 236 can be configured (e.g., trained, updated, fine-tuned, have transfer learning performed on) to have specializing language understanding, such as to perform the detection of the semantic feature(s) and/or target functions of the speech data 216. This can be performed, for example, in relation to a context, such as a given domain, of the speech to be detected by the at least one speech model 236. For example, the at least one speech model 236 can receive a context input indicating the domain. The system 200 can receive the context input as any one or more of text, audio, speech, image, and/or video data. In some implementations, the system 200 detects the context input based on an identifier of the electronic record 100, an identifier of a subject corresponding to the electronic record 100, or an identifier of a user of the electronic record interface 224, one or more of which the system 200 can map to a corresponding context input (e.g., where the electronic record 100 has an identifier that indicates the electronic record 100 is for dental procedures). In some implementations, the system 200 detects the context input based on the audio data 212 and/or speech data 216, such as to detect one or more keywords representative of context from the audio data 212.

The system 200 can apply the context input as input to the at least one speech model 236 to allow the at least one speech model 236 to generate the speech data 216 to have greater accuracy with respect to representing the actual content of the audio data 212. This can be useful in various applications described herein in which NLP systems may not properly disambiguate similar-sounding words or phrases in the audio data 212 in order to output a correct phrase for the speech data 216. For example, in general English, the word "museum" is spoken with much greater frequency than the term "mesial," while in the dental domain the word "mesial" is much more frequent than "museum." An NLP system configured to perform general speech detection would be likely often (if not always) transcribe audio for the term "mesial" as "museum." For example, at the level of generating confidence scores or other metrics for selecting amongst candidate speech outputs, an NLP system may determine a greater confidence score for "museum" than "mesial," resulting in an inaccurate speech data output. By using the context input to identify the domain for the audio data 212, the at least one speech model 236 can correctly output "mesial" as the speech data 216. As noted above, in some implementations, the training data for the at least one speech model 236 includes indications of context and/or domain, allowing the at least one speech model 236 to use context information at inference time. In some implementations, any of various training techniques are implemented to train the at least one speech model 236 to use the context inputs, such as conditioning, classifier-free guidance, and/or selective masking of the context information during training (e.g., training the at least one speech model 236 using a first subset of training data that includes context information, and using a second subset of training data that does not include context information).

In some implementations, an element of audio data 212 may include multiple commands (and/or values). The element can be, for example, a duration of audio data (e.g., of at least 2 seconds; of at least 5 seconds; of at least 10 seconds). As an example, the element of audio data 212 can include the phrases "jump to tooth 3, bleeding on tooth 3 all, skip tooth 4," having the commands "jump" and "skip" and value "bleeding on tooth 3 all." The at least one speech model 236 can detect boundaries between commands (and values) in the audio data 212, such as to detect that jump and skip are commands, where jump is associated with navigating to tooth 3, while the phrase "bleeding on tooth 3" references values to be assigned to the field for tooth 3, rather than an additional navigation command. In some implementations, the training data used to configure the at least one speech model 236 is labeled to correspondingly distinguish commands and values, allowing for the at least one speech model 236 to detect the boundaries. In some implementations, the at least one speech model 236 includes or is coupled with one or more rules to detect boundaries, such as rules to assign a greater confidence score to a number in the speech data 216 being part of a command where closer to the command text than farther than the command text (where more likely to be a value). In some implementations, the at least one speech model 236 detects the command (e.g., performs boundary detection) based at least on the context input.

The system 200 can include a record navigator 244. The record navigator 244 can be implemented using the front end application. The record navigator 244 can use the state data structure 232 and the speech data 216 to assign the speech data 216 to appropriate fields of the electronic record 100. For example, the record navigator 244 can determine which field(s) of the electronic record 100 to assign the subject data represented by the speech data 216. The record navigator 244 can include various rules, policies, heuristics, models, or logic to determine, based on the state represented by the state data structure 232 and the subject data represented by the speech data 216, which fields to assign the subject data to. For example, the record navigator 244 can include logic that if the speech data 216 includes a command of 'jump' and a location of '3' that a tab command should be entered three times in order to assign the subject data to tooth 3. As such, the front end application can write the subject data represented by the speech of the user into the electronic record 100 (e.g., into the electronic record interface 224, which can transmit the subject data to the subject database 204 to update the subject database 204).

As noted above, the electronic record 100 can be assigned at least one of structured or unstructured data. The record navigator 244 can detect context from the speech data 216 to identify (structured) fields to assign the speech data 216. The record navigator 244 can use the state monitor 228 to identify the fields to assign the speech data 216.

The system 200 can include a validator 248. The validator 248 can perform various error checking operations to improve the accuracy of assigning subject data to the electronic record 100. For example, the validator 248 can include various rules, policies, heuristics, models, or logic that can compare a command or data values indicated by the speech data 216 to expected commands or data values, and output an error responsive to the comparison not satisfying a comparison condition. For example, the validator 248 can include logic indicating that for each tooth, 3 values of pocket depths should be received, such that if the values and commands received through the speech data 216 are inconsistent with this logic, the validator 248 can output an error condition. This can improve operation of the system 200 by limiting instances in which errors may be detected subsequent to data entry (which can make it difficult to identify at which tooth or other state of the electronic record 100 the error originated from).

The system 200 can be used to perform treatment planning. For example, system 200 can retrieve, from the speech data 216, one or more treatment commands (e.g., using the at least one speech model 236 to identify the one or more treatment commands). The system 200 can use the at least one speech model 236 to identify keywords for initiating generation of a treatment plan. The system 200 can assign the one or more treatment commands to the electronic record 100. The electronic record 100 can include (or the system 200 can generate, responsive to the one or more treatment commands) a treatment plan template comprising one or more treatment plan fields, and the system 200 can use the state monitor 228 to identify treatment plan fields to which to assign the one or more treatment commands. For example, the state monitor 228 can determine, from the one or more treatment commands extracted from the speech data 216, a particular treatment plan field to assign a particular treatment command (e.g., using a model that indicates relationships between treatment plan fields and treatment commands as well as a current state of the treatment plan template). The system 200 can determine (e.g., from processing the speech data to identify the subject matter of the speech data) the treatment commands to be for charting commands to be treated, and can generate charts of existing conditions and treatments. This can enable treatment planning to be integrated into the PM, EHR, or other database itself, allowing for more rapid retrieval of the treatment plan for performing the treatment procedure and compartmentalizing the data of the treatment plan in the electronic record 100.

The system 200 can assign data associated with treatments or procedures to the electronic record 100. For example, the system 200 can process the audio data 212 to identify information such as clinical notes, procedure logs for surgical procedures or medical examinations (e.g., for various medical procedures, such as cardiological or orthopedic procedures), which can be assigned to the electronic record 100 (e.g., to particular fields for such information, or as unstructured data). The system 200 can determine a type of the information to assign the information to the electronic record 100.

The system 200 can provide feedback, such as audio feedback. For example, the system 200 can provide audio feedback using a user interface of the client device 220 to a user. The system 200 can provide the feedback based on at least one of the state and a request from the user. For example, the system 200 can use the state monitor 228 to monitor the state, and provide feedback responsive to the state corresponding to a predetermined state. For example, during a periodontal charting procedure, feedback can be provided responsive to the state being a midline state (e.g., a chime or other audio signal can be outputted responsive to a midline of the periodontal chart being crossed, allowing the user to track where they are in the procedure without needing to look at the electronic record). Responsive to a request for the feedback the system 200 can provide the feedback (e.g., using the voice processing engine 208 to detect a command requesting the feedback, such as a request to read back a most recent entry; a request to read back particular values (e.g., "what is the value of tooth number 10)). The system 200 can provide feedback to indicate an error (e.g., responsive to operation of the validator 248; responsive to determining that the state of the electronic record 100 does not match (e.g., a match score is less than a minimum match threshold) the provided speech data 216 expected to be assigned to a field corresponding to the state).

The system 200 can provide at least one report (e.g., using the client device 220). For example, the system 200 can aggregate or analyze the data of the electronic record 100 (e.g., using one or more functions, filters, rules, heuristics, or policies) to identify data elements of the electronic record 100 to include in a report. The system 200 can provide the report before, during, or after the procedure is performed on the subject. The system 200 can use a report template to assign data elements to the report. This can provide users with more digestible data, such as for use during the procedure.

The system 200 can use the client device 220 to present a training interface. The training interface can output at least one of image data (e.g., images, videos) or audio data (e.g., audio prompts) to indicate to a user how to operate the system 200 and request training inputs from the user. For example, the system 200 can output a request for a training input for a user to speak one or more particular words or phrases, and process audio data received in response to the request using various components of the system 200 (e.g., as described herein for processing audio data 212), including using the validator 248 to validate the received audio data to determine whether the user is providing inputs properly. For example, responsive to the validator 248 determining that the received audio data corresponds to the one or more particular words or phrases, the system 200 can determine that the audio data is correct (and output an indication that the audio data is correct); responsive to determining that the received audio data does not correspond to the one or more particular words or phrases, the system 200 can determine that the audio data is not correct (and output an indication that the audio data is not correct). The system 200 can use the audio data received in response to the request to train (e.g., further train) the at least one speech model 236.

The system 200 can process data using various tooth numbering systems or templates (e.g., for electronic dental records). For example, the system 200 can process data using the international tooth numbering system (1-1 to 1-8 . . . 4-1 to 4-8), as well as the US tooth numbering system (teeth numbered 1 to 32). The system 200 can process data using tooth numbering systems based on the voice processing engine 208 being trained using training data that includes speech data from each tooth numbering system. The system 200 can process the speech data 216 to detect the tooth numbering system (e.g., based on determining that a confidence that a pair of sequential numbers detected from the speech data 216 that corresponds to the international numbering system (e.g., detecting "1-1") at least one of meets a threshold or is greater than a confidence that the pair of numbers corresponds to values of a particular tooth in the US tooth numbering system. The system 200 can process data for various types of patients, such as pediatric or adult teeth systems (e.g., based on training data indicating numbering of such systems).

The system 200 can detect (e.g., using machine vision or other image processing of the electronic record 100, or responsive to user input indicating the tooth is missing) a variation of the electronic record 100 from a tooth numbering template, such as if a tooth of the subject is missing. Responsive to detecting the variation, the system 200 can process the values detected from the speech data 216 based on the variation, such as to skip assigning values to a missing tooth (e.g., responsive to detecting that tooth number 12 is missing, assign values for tooth number 11 to tooth number 11, and assign subsequent values to tooth number 13). Responsive to detecting user input indicating the variation, the system 200 can update the electronic record 100 to mark the tooth as missing.

The system 200 can process the speech data 216 and assign values to the electronic record 100 based on various orderings/paths through the teeth of the subject, such as from the buccal side of the mouth followed by lingual then lingual and back to buccal, and various other such paths. For example, the system 200 can receive user input indicating the path. The system 200 can detect the path based on maintaining a path state by the state monitor 228, which can be maintained and updated responsive to matching values indicative of the path state (e.g., sequence of tooth number values detected from the speech data 216) with expected values corresponding to the various paths (e.g., if a last buccal side tooth number is followed by a first lingual side tooth number, this can be indicative of a path from the buccal side to the lingual side). The system 200 can use the path state to modify at least one of a confidence value associated with a tooth number (or tooth value) detection by the at least one speech model 236 or the validator 248 or a threshold associated with a tooth number (or tooth value) detection by the at least one speech model 236 or the validator 248 (including if the user provides a "jump" command), enabling the system 200 to more accurately determine values to assign to the electronic record 100. The system 200 can use at least one of the path state and a tooth state maintained by the state monitor 228 to handle conditions such as moving past missing teeth and enabling a user to perform a read-back functionality (e.g., maintain a state indicative of a current tooth for which tooth values are being provided; responsive to detecting input from the speech data 216 indicating instructions to output values for a particular tooth, output the values for the particular tooth; responsive to outputting the values for the particular tooth, return to the current tooth for continuing to receive tooth values based on the at least one of the tooth state or the path state).

Referring further to FIG. 2, the electronic record interface 224 can be implemented using various components or applications of the client device 220, including but not limited to local applications, browser plugins, or browser extensions. The electronic record interface 224 can process a web-based representation of the subject record object 206, such as in HTML, CSS, XML, or other web-based data formats or data structures. For example, the electronic record interface 224 can retrieve HTML data representing the subject record object 206, such as HTML data received by the client device 220 to present the subject record object 206 using a browser application. The electronic record interface 224 can process the HTML data to identify particular elements of the subject record object 206 (e.g., based on comparing the HTML data or metadata thereof to predetermined templates or features for matching), such as fields representing the electronic record 100, such as representing a periodontal chart or other structured data of the electronic record 100 and/or subject record object 206.

To input and/or assign data to the subject record object 206 and/or the electronic record 100, the electronic record interface 224 can perform HTML processing operations such as HTML code manipulation, button clicks, and/or key presses. For example, the electronic record interface 224 can use a browser plugin or extension to read HTML values and the periodontal chart (or other charts or fields as requested) from the subject record object 206, and can apply at least one of HTML code manipulation, button click commands, or key press commands via respective input components of the client device 220 to input data to the subject record object 206 and/or the electronic record 100. The electronic record interface 224 can perform operations for input/output functions including to identify specific field(s) for receiving data from the subject record object 206 or assigning data to the subject record object 206, such as to detect data regarding particular teeth of the subject or values assigned to the fields representing the teeth (e.g., bleeding, suppuration, etc.); interacting with HTML buttons detected from the web-based representation of the subject record object 206, such as buttons for navigating fields or assigning values to fields (e.g., input a periodontal value or a label such as bleeding); and/or detecting a cursor location, which the electronic record interface 224 can process to detect the current tooth and/or state (e.g., using a template representing tooth and field locations of the subject record object 206 and/or electronic record 100). In some implementations, such as for a web extension and/or browser interface of the electronic record interface 224, the electronic record interface 224 can use a timer to facilitate timing of HTML element selection and corresponding input actions (e.g., button clicks and/or key presses). For example, responsive to receiving a command to enter a given phrase for a target field of the electronic record 100, the electronic record interface 224 can select the HTML element corresponding to the target field, initiate a timer indicative of an expected time for one or more key presses and/or button clicks to enter the given phrase, and delay initiation of a subsequent command (e.g., moving to a next field based on the next command in the detected speech data 216) until the time expires.

In some implementations, the electronic record interface 224 includes or is coupled with a local application, such as a native application operating separately from and/or in communication with a browser to present the electronic record 100 and/or the subject record object 206, as well as to provide inputs for updating the electronic record 100 and/or the subject record object 206. As discussed above, the electronic record interface 224 can apply computer vision operations to the representation of the electronic record 100 and/or the subject record object 206 to detect the fields, values, and state information, and can apply robotic process automation such as key presses and buttons clicks for input to the client device 220 to update the 100 and/or the subject record object 206. In some implementations, the electronic record interface 224 uses a Native library (e.g., NUTjs), to implement the robotic process automation. This can include, for example, assigning key presses in the EHR associated with the electronic record 100 to a corresponding keyboard shortcut customization of the EHR.

In some implementations, the system 200 establishes a network connection, such as a web socket connection, between the client device 220 that detects the audio data 212 (and which can implement the electronic record interface 224) and one or more other components of the system 200, such as the voice processing engine 208 (e.g., where the voice processing engine 208 is implemented in a cloud and/or server system). The client device 220 can provide the audio data 212 to the voice processing engine 208 in various formats, such as unstructured data formats (e.g., blobs of raw data representative of speech over a period of time). The voice processing engine 208 can provide a response (e.g., in JSON format) that includes the speech data 216 and/or an intent represented by the speech data 216 to the electronic record interface 224 responsive to processing the audio data 212. The response can include a data structure to represent the speech data 216, such as to have data elements for one or more of restorative procedure, condition name, tooth number, and tooth surface.

The electronic record interface 224 can update the electronic record 100 based at least on the response, such as to align the electronic record 100 with instructions represented by the speech data 216. As noted above, the electronic record interface 224 can perform HTML operations on the electronic record 100 to read data of the electronic record 100 (e.g., to identify fields of the electronic record 100) and update the electronic record 100. For example, responsive to the response indicating to "apply root canal on tooth number 3," the electronic record interface 224 can access, based on the identifier of tooth number 3, the HTML document object model (DOM) element corresponding to tooth number 3, identify the "add procedure" input element corresponding to the DOM element for tooth number 3, input text data such as "root canal therapy on anterior/posterior/molar" in the procedure search box, and execute the procedure. In some implementations, the electronic record interface 224 detects a tooth type corresponding to the tooth number, and assigns a code (e.g., American Dental Association (ADA) code) corresponding to the tooth type to the electronic record 100.

In some implementations, the electronic record interface 224 selects (and executes) at least one initiation action based at least on the command represented by the speech data 216 (e.g., even if the speech data 216 does not explicitly identify the initiation action). The initiation action can include, for example, commands for selecting a type of data entry process or to select a procedure code listbox for further interaction. For example, responsive to determining that the speech data 216 represents a command to "add root canal on tooth number 3," the electronic record interface 224 can select and execute initiation action(s) including at least one of selecting the operation as a "set existing" operation or causing navigation to the procedure code listbox for selection of a code corresponding to the command, prior to execution of the command (e.g., prior to causing navigation to the field for tooth number 3 and data entry at the field for tooth number 3, where the data entry can include entering the selected code).

Figure 3:
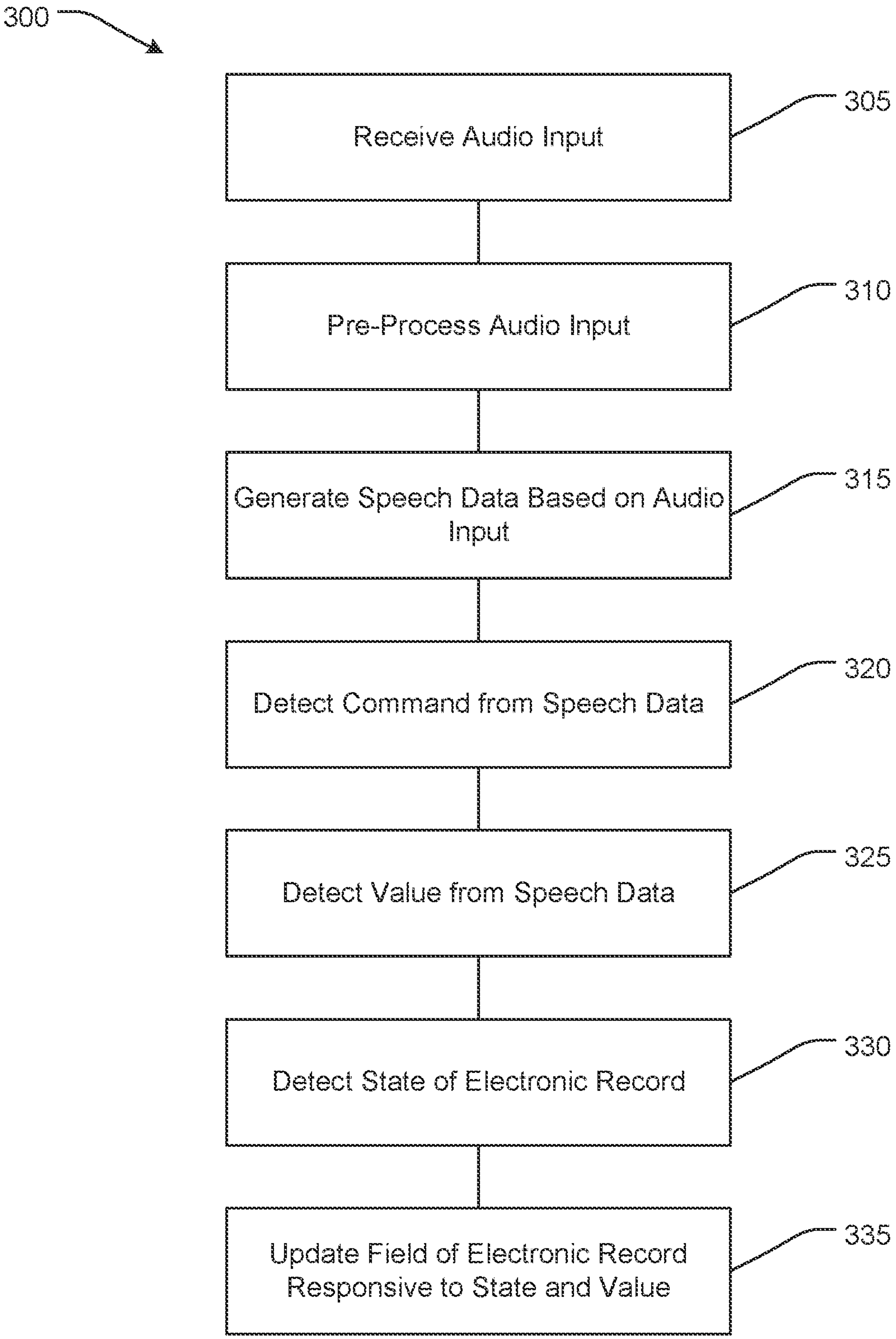
FIG. 3 depicts a flow diagram of a method for operating an electronic record voice assistant system.

FIG. 3 depicts a method 300 of operating an electronic record voice assistant system. The method 300 can be performed using various systems and devices described herein, including the electronic record 100 described with reference to FIG. 1, the system 200 described with reference to FIG. 2, and the computing device 1000 and associated computing environment described with reference to FIGS. 10A and 10B. The method 300 can be used to perform real-time or batch processing of medical procedure data to accurately update an electronic record of a subject.

The method 300 can include receiving an audio input (305). The audio input can be indicative of a command. The audio input can be received via an audio input device (e.g., microphone) of a client device. The audio input can be received based on a user navigating to a webpage that connects with an electronic health record system. The audio input can represent speech that can be processed as described herein to detect a verbal command (e.g., user voice command), such as "jump to tooth number 3."

The method 300 can include pre-processing the audio input (310). For example, the audio input can be filtered or compressed for further processing. The audio input can be pre-processed by an application implemented by the client device, and transmitted to a remote device (e.g., cloud-based server) for further processing. The audio input can be transmitted as an audio stream to the remote device.

The method 300 can include generating speech data (e.g., text representative of the audio input) based on the audio input (315). The speech data can be generated by providing the audio input as an input to at least one speech model, such as a machine learning model (e.g., neural network) trained using domain-specific audio and vocabulary. The speech data can be generated by a voice processing engine implemented by the remote device (e.g., cloud-based server) to convert the audio data into text data.

The method 300 can include detecting at least one command from the speech data (320). For example, a natural language processor can be applied to the speech data to detect the at least one command. The at least one command can be representative of an intent. The at least one command can be representative of an action for selecting a field of the electronic record to which to assign subject data. The at least one command can be determined based on at least one value detected from the speech data. In some implementations, the at least one command is not detected from the speech data (e.g., the speech data may not include a command, the speech data may not be processed to detect a command, or the at least one command may be determined from the at least one value, rather than from the speech data).

The method 300 can include detecting at least one value from the speech data to be assigned to a field of the electronic record (325). The at least one value can be extracted from the speech data or from phrases determined from the speech data. For example, a natural language processor can be applied to the speech data to detect the at least one value. The at least one command (e.g., "jump") and the at least one value (e.g., "tooth 3") can form a response to be provided to the application implemented by the client device. The at least one value can represent a pauseless multicomponent (e.g., multicommand) input.

The method 300 can include detecting a state of the electronic record (330). The state can be a particular field of the electronic record that is currently selected or at which data was most recently entered. The state can be maintained in a state data structure (e.g., by the application implemented by the client device).

The method 300 can include updating a particular field of the electronic record using the at least one value, and the state (335). Updating the particular field can include updating the particular based on the at least one command, the at least one value, and the state. For example, the state can be used to identify the particular field, such as a field associated with a tooth indicated by the speech data (e.g., a tooth to move to based on the state and the at least one value, the at least one command, or a combination thereof). Updating the particular field can include causing an application that implements the electronic record on the client device to transmit the update to the electronic record to a server that maintains a subject database that includes the electronic record. The application implemented on the client device can provide inputs to the electronic record (e.g., an application that implements the electronic record) to move through a structure of the electronic record to select the particular field; for example, the application can determine to provide a tab keystroke input three times in order to jump to tooth 3. Updating the electronic record can cause the presentation of the electronic record to be updated, enabling the user to see the updates (e.g., see the value assigned to tooth 3). Updating the electronic record can include transmitting a representation of the electronic record (or values thereof) to the server to cause the server to update the subject database. The electronic record can be updated asynchronously. The electronic record can be updated in real time, or in a batch process (e.g., at the end of an examination; at regular intervals, such as hourly or daily).

Figure 4:
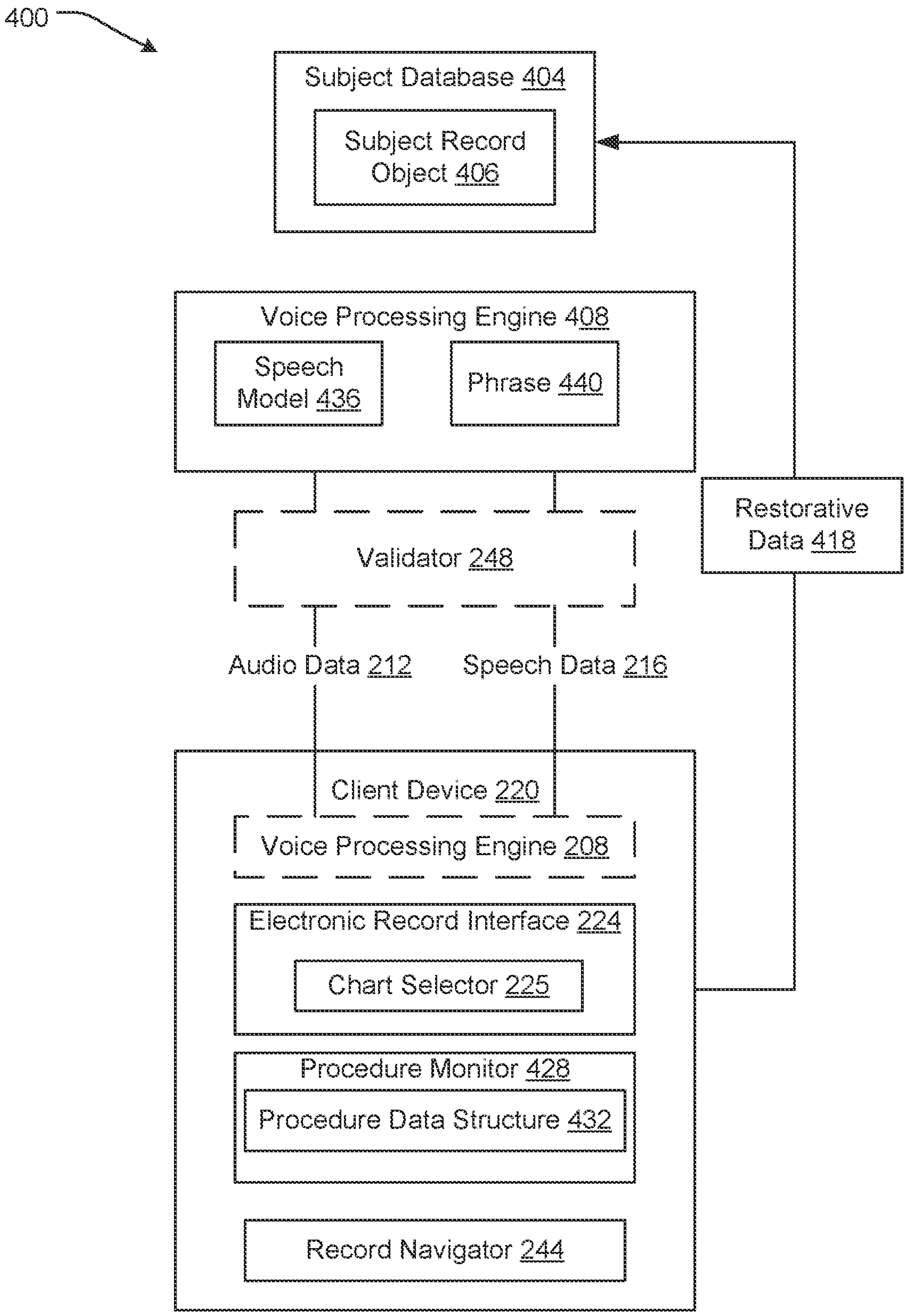
FIG. 4 depicts a block diagram of an example of an electronic record voice assistant system.

FIG. 4 depicts a block diagram of an example of a system 400. The system 400 can incorporate various features of the system 200 as described with reference to FIG. 2, and can have features that are similar or identical to those of system 200. The system 400 and components thereof can be implemented using various features of the computing environment 1000 described with reference to FIGS. 10A-10B.

The system 400 can be used to implement a voice assistant, such as for speech processing operations, for various procedures, including dental procedures. As described further herein, the system 400 can include a voice processing engine 408, which can be configured to detect speech data (e.g., as phrases 440) for assigning to subject data record 406 with high accuracy, precision, and recall, such as by being trained using training data that is labeled with and/or conditioned on indications of audio and speech that is relevant for (or not relevant for) assigning to the subject data record 406. Dental procedures can include a variety of procedures, including restorative procedures, such as to provide tooth fillings, extractions, root canals, crowns, implants, and bridges. The subject data record 406 can include fields for assigning information such as medical history and planned procedures. The medical history can include information such as current health of the mouth or teeth, existing tooth decay, abscesses, past tooth fillings, existing implants, root canals, or crowns, or various combinations thereof. The procedure information can include information such as minor or major restorative planned procedures, such as fillings, root canals, crowns, implants, or bridges.

Electronic tools, such as voice assistants, can receive the subject data in order to provide the subject data to the database. As such, these procedures can be of relatively long duration, and there may be conversational dialogues or other speech occurring during the procedures that is not to be documented or otherwise recorded in the electronic health record. As such, there can be a relatively large amount of noise during the procedure, including such speech that is detectable during the procedure yet is not to be assigned to the electronic health record. As described further herein, the system 400 can be configured to handle these types of signal/noise considerations, including by how the voice processing engine 408 is trained and/or through the use of state monitoring, to meet accuracy, precision, and/or recall criteria.

Referring further to FIG. 4, the system 400 can include a subject database 404, which can be similar to the subject database 204. The subject database 404 can store and maintain record objects 406 for various subjects. The record objects 406 can include the electronic record 100 and features thereof described with reference to FIG. 1. The record objects 406 can include subject profile data, such as name, age, or date of birth, height, weight, sex, and medical history information. The record objects 406 can include dental data regarding a subject. For example, for one or more teeth of the subject, the record object 406 can include an identifier of the tooth and one or more values assigned to the tooth. The one or more values can include, for example, values for fields such as whether (and which) treatments have been previously performed on the tooth.

The system 400 can include a voice processing engine 408, which can include features of the voice processing engine 208 described with reference to FIG. 2. For example, the voice processing engine 408 can include at least one speech model 436, which can be implemented in a similar manner as the speech model 236. The speech model 436 can be trained using training data representative of audio and/or speech information (e.g., recorded or transcribed dialogues) of procedures, such as dental procedures. The training data can include examples of information recorded in subject data records associated with audio and/or speech from procedures, as well as specific fields to which values are assigned, enabling the speech model 436 to be trained to determine information to assign to the record objects 406 (e.g., even in high noise situations).

The system 400 can determine a state of at least one of a tooth or a gingiva (e.g., gum) of a subject by processing an electronic record 100 associated with the subject, which may correspond with a record object 406. The system 400 can retrieve the record object 406 and can process the record objects 406 to identify a field corresponding to at least one tooth. For example, the system 400 can perform one or more operations as described for system 200 with respect to FIG. 2 to retrieve data from the record objects 406 and/or particular fields thereof, including but not limited to applying computer vision and/or HTML processing or other processing of the subject record object 406.

The system 400 can determine the tooth for which to retrieve data. For example, the system 400 can retrieve a tooth index from the electronic record 100. The system 400 can process the tooth index numerically. The system 400 can receive audio input from a user to retrieve data for the tooth. The system 400 can process the audio input using the voice processing engine 408, and retrieve data from the record objects 406. The system 400 can determine the tooth for which to retrieve data according to a stored state. The system 400 can determine the tooth for which to retrieve data according to a previously accessed state. The system 400 can determine the tooth for which to retrieve data by identifying teeth that have previously been labeled with procedures or treatments in the record objects 406.

The system 400 can determine the state by processing various fields of the electronic record 100. For example, the electronic record 100 may have a field labeled as state, or a field having values indicative of state information (e.g., based on predetermined keywords, rules, policies, or configuration of the speech model 436 based on training data mapping values to state information). The system 400 can process the electronic record 100, identify the field labeled as state, process the field to identify the keywords relating to state, and determine the state of at least one tooth according to the state field of the electronic record 100. An example of the state of at least one tooth can be to determine what procedures, if any, have been performed on the at least one tooth. An example of a procedure can be a minor restorative procedure. Examples of a minor restorative procedure can include a filling and a root canal. An example of a procedure can be a major restorative procedure. Examples of a major restorative procedure can include a crown, an implant, and a bridge. The state can be a labeling of new treatments to be performed. The system 400 can determine the state by processing various fields of the subject database 404. The system 400 can determine the state by retrieving procedure history data from the subject database 404. For example, procedure history data can include information about the health of the subject's mouth. Procedure history data can include information about tooth decay. Procedure history data can include information about abscesses in the subject's mouth. Procedure history data can be information about what procedures have been performed on the tooth.

The system 400 can include a procedure monitor 428. The procedure monitor 428 can determine, based at least on the state, a procedure to be applied to the at least one tooth. The procedure monitor 428 can determine the state based at least on a previous value of the state.

For example, the procedure monitor 428 can determine the previous state for the at least one tooth of a root canal treatment. Based at least on this determination, the procedure monitor 428 can determine the state to be repair of crown. For example, the procedure monitor 428 can determine the old state for the at least one tooth of a cavity. Based at least on this determination, the procedure monitor 428 can determine the state to be repair of cavity. The procedure monitor 428 can determine, based at least on the procedure history data, a procedure to be applied to the tooth. For example, if the procedure monitor 428 determines there is tooth decay from the medical history data, the procedure monitor 428 can determine based, at least in part, on the determination of a history of tooth decay, the procedure to be applied is a cavity filling.

The procedure monitor 428 can include and maintain a procedure data structure 432 of the electronic record interface 224 as described in FIG. 2. The procedure data structure 432 can be a data structure that includes a state (e.g., current location) in the electronic record 100 implemented by the electronic record interface 224 as described in FIG. 2. For example, the procedure data structure 432 can include fields indicating values of the state such as a tooth and a side of the tooth. For example, the procedure data structure 432 can include fields corresponding to fields of the chart data object 104 as described in FIG. 1, such as a tooth field (e.g., the tooth field can have a value of "2" to indicate that it is tooth number 2) a side field (e.g., the side field can have a value of "buccal" to indicate the buccal side of the tooth), a state field (e.g., the state field can have a value of "cavity" to indicate the tooth has a cavity), and a last procedure field (e.g., the last procedure field can have a value of "root canal" to indicate the last procedure performed on the tooth was a root canal).

The procedure monitor 428 can select the procedure from a plurality of procedures and assign a flag from a plurality of flags to the electronic record 100 based at least on the selection of the procedure. The procedure monitor 428 can determine the procedure by applying the state to a data structure that maps a plurality of procedures with a plurality of states. For example, the procedure monitor 428 can determine the procedure by applying the state to a look up table and selecting the procedure from a plurality of procedures that match to the state. The procedure monitor 428 can rank the plurality of procedures by assigning flags from the plurality of flags to indicate which procedures from the plurality of procedures are more likely to be applied to the tooth. For example, based at least in part of a determination by the system 400 that the state of the tooth is "cavity," the procedure monitor can apply the state "cavity" to a data structure (e.g., a lookup table). The data structure can map a plurality of procedures that correlate to the state, such as "filling" and "crown" that can map to "cavity." The procedure monitor 428 can then assign a first flag to "filling" to indicate it is the most likely procedure to be applied to the tooth, and a second flag to "crown" to indicate it is the second most likely procedure to be applied to the tooth.

Referring further to FIG. 4, the voice processing engine 408 can receive audio data 212 and process the audio data 212 to detect speech data 216 from the audio data. The audio data 212 can be retrieved in real-time or near real-time, or can be stored and retrieved at a subsequent time for processing (e.g., for batch processing). The voice processing engine 208 can include at least one speech model 436. The speech model 436 can be a machine learning model trained to generate the speech data 216 responsive to the audio data 212. The speech model 436 can be trained to accurately determine speech data 216 from audio data 212 that has high volumes of noise. Noise can be components of the audio data 212 that are not relevant to the procedure. Noise can be sounds that distort the audio data. For example, noise can be sounds created by medical instruments. Noise can be speech in the audio data that is unrelated to the procedure being applied to the tooth. The speech model 436 can be trained to determine that speech not relevant to the procedure is not to be assigned to the subject record object 406, and can effectively filter out such speech (e.g., based on being trained using training data having high volumes of noise).

The voice processing engine 408 can provide the audio data 212 to the at least one speech model 436 to cause the at least one speech model 436 to generate at least one phrase 440. The phrase 440 can be a subset of the speech data 216. The phrase 440 can be relevant to the procedure being applied to the tooth. The speech model 436 can assign a confidence value (e.g., confidence score, probability score) to each phrase 440. The confidence value can indicate an expectation of the accuracy of the phrase 440 in representing the true information (e.g., true speech or correct speech) of the audio data 212. The confidence value can be based at least on the state determined by the system 400. In some implementations, the voice processing engine 408 can determine a plurality of candidate phrases 440 from the audio data 212, can assign a confidence score to each candidate phrase of the plurality of candidate phrases 440 based on at least one of (i) the (current) state of the tooth or (ii) the procedure being applied to the tooth, and can select a particular candidate phrase of the plurality of candidate phrases 440 (e.g., for output; for assignment to the subject data record 406) according to the respective confidence scores assigned to the candidate phrases. The system 400 can detect relationships between the states, procedures, and phrases, for determining confidence scores for particular phrases, by having been trained using training data representative of various such relationships and/or by implementing, in the voice processing engine 408, various rules, policies, heuristics, or combinations thereof that map phrases to states and/or procedures.

For example, the phrase "cavity filling" can receive a high confidence score responsive to the system 400 identifying the state to be "cavity," but a low confidence score responsive to the system 400 identifying the state to be "root canal." The confidence score can be based at least on the procedure determined by the procedure monitor 428 to be applied to the at least one tooth. For example, the phrase "abscess" can receive a high confidence score responsive to the system 400 determining the procedure to be applied to the tooth as "root canal," but a low confidence score responsive to the system 400 determining the procedure to be a cavity filling.

The system 400 can receive audio data 212 during the procedure. The system 400 can receive audio data 212 prior to the procedure. The audio data 212 received by the system 400 can be first audio data. The audio data received by the system 400 prior to the procedure can be second audio data. The voice processing engine 208 can apply the second audio data to at least one speech model 436 do determine medical history data representative of the second audio data based at least on a medical history of the subject. The medical history data can include information on past procedures applied to at least one tooth of the subject. The medical history data can include information such as the height, weight, sex, age, and allergies of the subject. The procedure monitor 428 can determine, based at least in part on the medical history data, the procedure to be applied to the tooth. For example, if the voice processing engine 208 determined the presence of a large crack in a tooth from the medical history data, the procedure monitor could determine, based at least in part on the presence of the large crack, that the procedure to be applied to the tooth was a crown.

The system 400 can determine medical recommendation data from the speech data 216 (e.g., medical recommendation data can be a subset of speech data). Medical recommendation data can be treatment plan data (e.g., instructions for the subject after the procedure has concluded). For example, medical recommendation data can include dietary restrictions, such as "liquid or semi-solid diet," or "no food for the next 2-4 hours." Medical recommendation data can include instructions for pain management, such as "take two 500 mg caplets of Tylenol every 4-6 hours," or "take the prescribed painkiller once every 8 hours." Medical recommendation data can include precautionary instructions, such as "call us if the bleeding does not stop within the next day" or "call us if the swelling returns."

The system 400 can determine commands from the speech data 216 (e.g., commands can be a subset of speech data). Commands can be details about at least one procedure that was performed on at least one tooth, for example, a command can be "amalgam filling on tooth no 5 occlusal, class IV." A command can be an observation about at least one tooth, for example "zirconia crown present on tooth number 8." A command can be a future treatment or procedure plan for at least one tooth, for example "prophylaxis planned on 3$^{rd}$ sextant."

The system 400 can assign speech data 216 (e.g., detected phrases 440) to the electronic record 100. The system 400 can assign one or more subsets of speech data 216 to the electronic record. For example, the system can assign medical history data, medical recommendation data, commands, and phrases to the electronic record 100. The electronic record 100 can be updated according to a command. Medical recommendation data can be assigned to the electronic record 100. Medical history data can be assigned to the electronic record 100. Data that are assigned to the electronic record 100 can be referred to as restorative data. The system 400 can assign restorative data 418 to a plurality of fields of the electronic record 100. The system 400 can assign data to appropriate fields in databases including but not limited to PM, HER, EMR, electronic dental record, CRM, and ERP databases. For example, the system 400 can assign restorative data 418 that is structured (e.g., data expected to be assigned to particular respective fields) to the electronic record 100. For example, the system 400 can assign unstructured data (e.g., data corresponding to streams of text that can be assigned to various fields) to the electronic record. The system 400 can assign structured data such as notes into an ERP database. The record navigator 244 as referenced in FIG. 2 can detect context from the speech data 216 to identify (structured) fields to assign the speech data 216. The record navigator 244 can use the procedure monitor 428 to identify the fields and assign the speech data. The system 400 can include the validator 248 as referenced in FIG. 2 to perform various error checking operations to improve the accuracy of assigning subject data to the electronic record 100.

Figure 5:
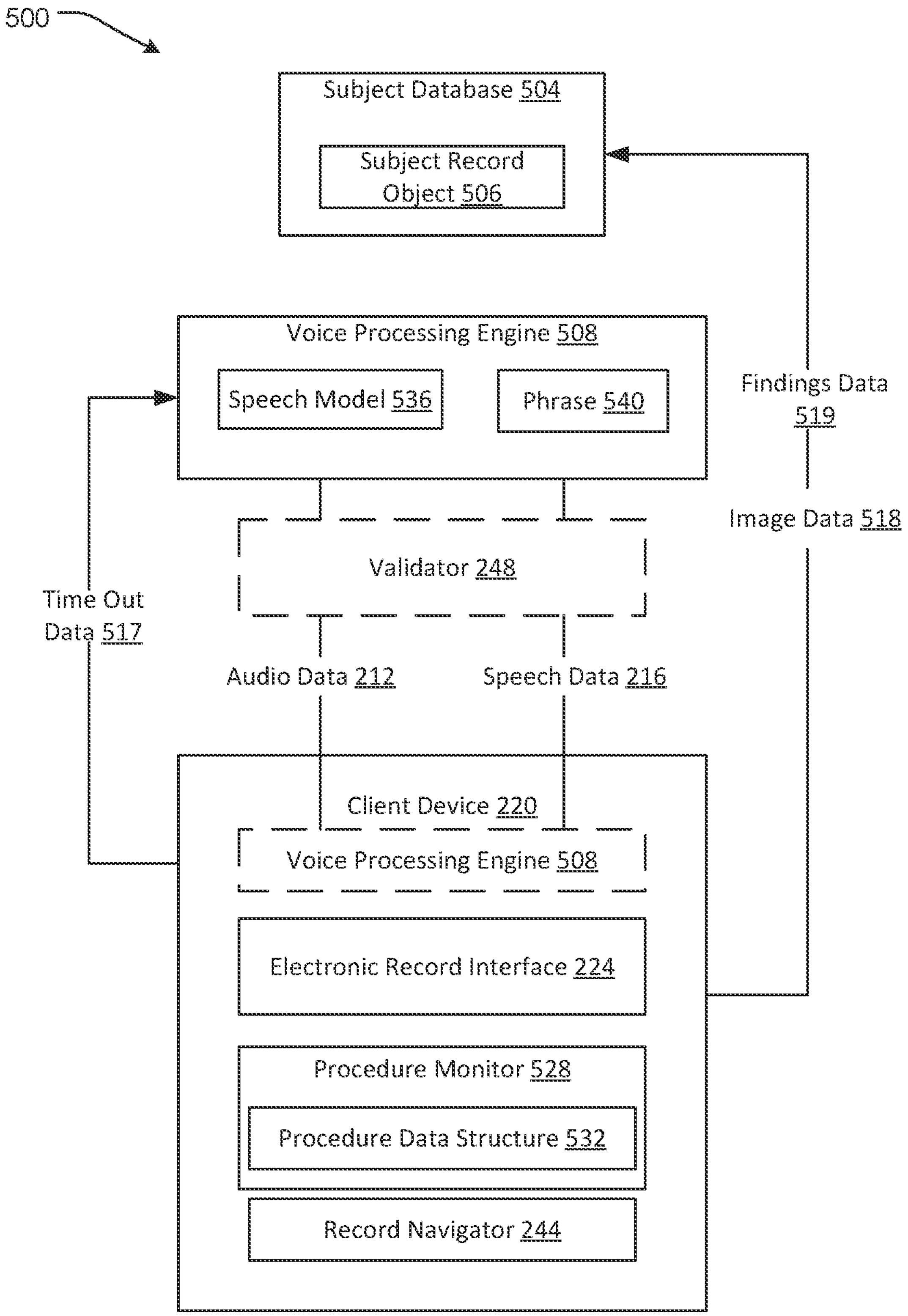
FIG. 5 depicts a block diagram of an example of an electronic record voice assistant system.

FIG. 5 depicts an example of a system 500 for implementing a voice assistant, including for endoscopic procedures, such as gastrointestinal procedures. The system 500 can incorporate features similar or identical to those of various systems described herein, including but not limited to the systems 200, 400. Various operations of the system 500 can be implemented using the computing device 700.

As noted above, procedures such as colonoscopies and endoscopies can be performed for a relatively long period of time, such as between 20-30 minutes. During the procedure, the person performing the procedure can search for abnormalities in the searched area, such as in the colon, esophagus, and surrounding organs. Various findings can be documented in the electronic health record (e.g., in subject data record 508). Findings can be biopsied and sent to a pathology lab, which can require the specimen to be stored and labeled. To facilitate proper documentation, time stamps relating to findings can be marked in these procedures. For example, the phrase "scope in" can be said to mark a time when a scope enters the body, "extent reached" can be used to indicate the maximum extent of the scope has been reached, and "scope out" can be used to indicate the scope has exited the body. Another phrase that can require time stamp data is the phrase "polyp found" to indicate an abnormal finding. Other forms of data that can be entered into the electronic health record include recommendations and impressions. Data can be entered into the electronic health record before, during, or after the procedure, and this process can be time consuming as well as error prone. Gastrointestinal records and databases can include or operate with electronic medical records, electronic gastrointestinal records, practice management systems, treatment planning, and patient charting software. In some instances, the procedures may be relatively noisy, such as due to conversations or other dialogue occurring during the procedures that may not necessary be relevant for documentation or recording to the subject data record 508 or other electronic health records. In various such use cases, the system 500 can effectively detect speech data for assigning to the subject data record 508 while not assigning information that may not be relevant for documentation.

The system 500 can include or be coupled with a subject database 504, which can include a plurality of subject record objects 506. The subject record objects 506 can correspond to subjects for which procedures, such as gastrointestinal procedures or other procedures that may involve camera, ultrasound, or other imaging or real-time information detection regarding the subjects, are to be performed.

The system 500 can determine (e.g., using electronic record interface 224 and/or procedure state monitor 528) a state of the subject based on the subject record object 506. For example, the system 500 can parse the subject record object 506 to identify one or more fields indicative of the state, such as fields indicating a condition of the subject or a procedure to be performed on the subject.

The system 500 can include a voice processing engine 508, which can be similar to, incorporate features of, and/or be trained in a similar manner as various voice processing engines described herein, such as the voice processing engines 208, 408. The voice processing engine 508 can include a speech model 536, which can be similar to the speech models 236, 436. The speech model 536 can include one or more machine learning models (e.g., neural network models) that are configured using training data relating to procedures performed on subjects. For example, the training data can include one or more training data examples that include audio data from a procedure and at least one of (i) speech detected from the procedure or (ii) information recorded to a subject data record from the procedure. For example, the training data examples can include audio data, detected speech data, and an example data record indicating speech assigned to particular portions (e.g., fields, unstructured data entry portions) of the example data record. In some implementations, at least one of the state or an identifier of the procedure being performed is included in the training data example, which can enable the speech model 536 to be trained to more accurately identify speech that corresponds with specific procedures and/or events during procedures (e.g., by monitoring speech detected during procedures).

The voice processing engine 508 can receive audio data 212 and apply the audio data 212 as input to the speech model 536 to determine speech data 216, such as phrases 540. In some implementations, the voice processing engine 508 applies the audio data 212 and at least one of the state or the identifier of the procedure as input to the speech model 536 together with the audio data 212. The voice processing engine 508 can determine the speech data 216 in real-time or near real-time, such as by receiving the audio data 212 (e.g., in batches of audio over a period time) during the procedure and processing the audio data 212 responsive to receiving the audio data 212. In some implementations, the voice processing engine 508 determines the speech data 216 at least partially after completion of the procedure. Responsive to completion of processing of the audio data 212 (e.g., reaching an end time of the audio data 212), the electronic record interface 224 can evaluate the subject data record 506 to determine one or more missing fields (e.g., fields not having values assigned from the procedure), and can assign a flag to the one or more missing fields to highlight for completion by a user.

The voice processing engine 508 can determine a procedure state of the procedure based on the speech data 216, and can assign the procedure state to a procedure state data structure 532. For example, the voice processing engine 508 can identify keywords of the speech data 216 corresponding to the procedure state, such as keywords relating to anatomical features associated with the procedure (e.g., features of the colon for endoscopic or gastrointestinal procedures), or keywords such as "scope in," "scope out," "extent reached," or "polyp found." The voice processing engine 508 can identify the keywords using a data structure, such as a lookup table, that indicates keywords for the procedure. The voice processing engine 508 can evaluate the speech data 216 to periodically identify and/or update the procedure state, such as by evaluating each detected word, or a subset of detected words (e.g., according to a schedule of when to evaluate detected speech data 216 for keywords) to determine and/or update the procedure state.

The voice processing engine 508 can determine the speech data 216 using the procedure state. For example, the voice processing engine 508 can apply the procedure state as input to the speech model 536 (e.g., as the state; together with the audio data 212; together with the audio data 212 and the identifier of the procedure). In some implementations, the voice processing engine 508 determines the speech data 216 using the procedure state for at least one of (i) a predetermined duration subsequent to determining the procedure state or (ii) until an update of the procedure state as determined by the system 500. This can enable the voice processing engine 508 to use the procedure state to more accurately determine the speech data 216. In some implementations, the voice processing engine 508 determines a confidence score (e.g., confidence value, probability score) of each of a plurality of candidate speech data (e.g., candidate phrases 540) based on at least one of the state, the identifier of the procedure, or the procedure state, and determines the speech data 216 according to the respective confidence scores. For example, the voice processing engine 508 can select a candidate speech data of the plurality of candidate speech data having the highest confidence score as the detected speech data 216. For example, responsive to determining the procedure state to relate to the keyword "polyp," the voice processing engine 508 can determine relatively higher confidence scores for candidate speech data relating to features of polyps rather than candidate speech data relating to initial steps of the procedure.

The voice processing engine 508 can assign the speech data 216 to the subject data record 506 based on at least one of the state (e.g., state of the subject) or the procedure state. For example, the voice processing engine 508 can identify, based on one or more keywords of the speech data 216, a corresponding field of the subject data record 506 to which to assign the speech data 216. The voice processing engine 508 can determine whether to assign the speech data 216 based on the training of the speech model 536 (e.g., based on training examples indicating examples of speech that is assigned to electronic records or is not assigned to electronic records).

Referring further to FIG. 5, the system 500 can detect, by processing the audio data 212 during the procedure using the voice processing engine 508, one or more findings data 519. The findings can indicate anatomical features of the subject for documentation and/or sample extraction. The voice processing engine 508 can identify one or more characteristics of the findings. For example, findings can include polyps and/or conditions (e.g., diverticulitis, ulcer), and the system 500 can identify characteristics of the findings such as location (e.g., sigmoid colon), size (e.g., 100 millimeters), type (e.g., sessile, semi-sessile), removal technique (e.g., cold snare), whether it was resected (e.g., resected/not resected), or various combinations thereof. The subject data record 506 may have a template of fields that the system 500 can identify (e.g., using computer vision, HTML processing, etc.) and match with the values of the speech data 216 corresponding to the findings to assign the values to respective fields. In some implementations, the system 500 detects time outs 517 ("cecum reached," "max extent reached," "scope in," "scope out") and can determine at least one of the procedure state or the speech data 216 based on the detected time outs. The system 500 can determine, based on the characteristics of the findings, text to assign to a label for the finding (e.g., for labeling a jar in which a sample of the finding is captured), such as text including one or more of the characteristics of the finding determined from the speech data 216.

In some implementations, the system 500 detects speech data 216 indicative of an image location. For example, various procedures may be performed with imaging equipment (e.g., camera, ultrasound, etc.). The system 500 can detect, from the speech data 216, a keyword corresponding to image capture (e.g., "image captured in the cecum"), and identify a time stamp associated with the detection (e.g., a period of time since the start of the procedure and/or since the start of a procedure state, e.g. since detecting the speech "scope in" or speech indicative of the start of image recording). The system 500 can match, based on the time stamp, the speech data 216 corresponding to the image capture with image data 518, such as an image captured at or proximate the time of the time stamp, enabling auto-labeling of images. For example, an endoscope used to perform the procedure may include an image capture device, and the system 500 can receive one or more images from the image capture device and match the speech data 216 with the one or more images.

The system 500 can assign detected speech data 216 to one or more recommendation fields. For example, the subject data record 506 can include a field indicative of recommendations regarding follow-up treatment, medications, or subsequent procedures to be performed. The voice processing engine 508, having been trained using example data records, can determine to assign speech data 216 for recommendations (e.g., "high fiber diet;" "no aspirin for 7 days") to the one or more recommendation fields.

Figure 6:
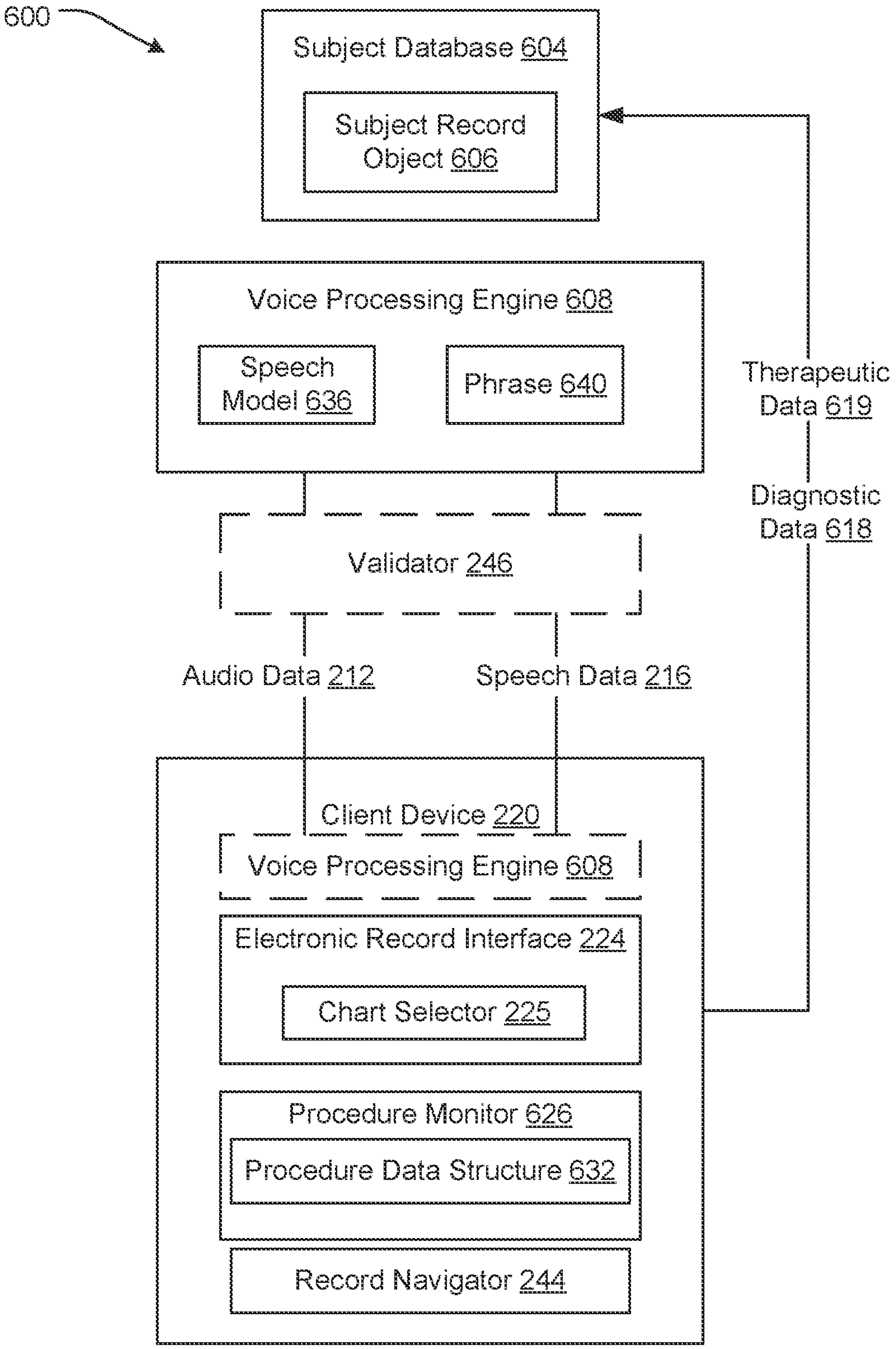
FIG. 6 depicts a block diagram of an example of an electronic record voice assistant system.

FIG. 6 depicts an example of a system 600 for implementing a voice assistant, including for cardiological procedures, such as catherization or electrophysiological procedures. The system 600 can incorporate features similar or identical to those of various systems described herein, including but not limited to the systems 200, 400, 500. Various operations of the system 600 can be implemented using the computing device 700.

As noted above, cardiac or cardiological procedures such as catherizations, electrophysiological procedures, stent insertions and deployments, angiograms, pacemaker insertions and deployments, among others, can involve relatively long periods of time during which relatively large amounts of speech may occur, including speech that represents information to include as findings for a coronary report. For example, physicians and their teams may conduct frequent cardiac catheterization & electrophysiology procedures (e.g. 10/day/room), which may each one be performed for around 30-60 minutes. During some procedures the physicians may be inserting a stent (sometimes along with a balloon) into the subject and measuring the blockage (stenosis) in different arteries and blood vessels. In some procedures the speech may be indicative of diagnoses and/or therapeutic actions or recommendations.

The system 600 can include or be coupled with a subject database 604, which can include a plurality of subject record objects 606. The subject record objects 606 can correspond to subjects for which procedures, such as cardiac or cardiological procedures, are to be performed. Various such procedures may involve using sensors and/or imaging devices to detect information regarding the subjects during the procedures, such as positions of components or implants, blood flow, or other information associated with the procedures.

The system 600 can determine (e.g., using electronic record interface 224 and/or procedure state monitor 628) a state of the subject based on the subject record object 606. For example, the system 600 can parse the subject record object 606 to identify one or more fields indicative of the state, such as fields indicating a condition of the subject or a procedure to be performed on the subject.

The system 600 can include a voice processing engine 608, which can be similar to, incorporate features of, and/or be trained in a similar manner as various voice processing engines described herein, such as the voice processing engines 608, 608. The voice processing engine 608 can include a speech model 636, which can be similar to the speech models 236, 436, 536. The speech model 636 can include one or more machine learning models (e.g., neural network models) that are configured using training data relating to procedures performed on subjects. For example, the training data can include one or more training data examples that include audio data from a procedure and at least one of (i) speech detected from the procedure or (ii) information recorded to a subject data record from the procedure. For example, the training data examples can include audio data, detected speech data, and an example data record indicating speech assigned to particular portions (e.g., fields, unstructured data entry portions) of the example data record. In some implementations, at least one of the state or an identifier of the procedure being performed is included in the training data example, which can enable the speech model 636 to be trained to more accurately identify speech that corresponds with specific procedures and/or events during procedures (e.g., by monitoring speech detected during procedures).

The voice processing engine 608 can receive audio data 212 and apply the audio data 212 as input to the speech model 636 to determine speech data 216, such as phrases 640. In some implementations, the voice processing engine 608 applies the audio data 212 and at least one of the state or the identifier of the procedure as input to the speech model 636 together with the audio data 212. The voice processing engine 608 can determine the speech data 216 in real-time or near real-time, such as by receiving the audio data 212 (e.g., in batches of audio over a period time) during the procedure and processing the audio data 212 responsive to receiving the audio data 212. In some implementations, the voice processing engine 608 determines the speech data 216 at least partially after completion of the procedure. Responsive to completion of processing of the audio data 212 (e.g., reaching an end time of the audio data 212), the electronic record interface 224 can evaluate the subject data record 606 to determine one or more missing fields (e.g., fields not having values assigned from the procedure), and can assign a flag to the one or more missing fields to highlight for completion by a user.

The voice processing engine 608 can determine a procedure state of the procedure based on the speech data 216, and can assign the procedure state to a procedure state data structure 632. For example, the voice processing engine 608 can identify keywords of the speech data 216 corresponding to the procedure state, such as keywords associated with cardiological anatomical features (e.g., specific blood vessels and/or blockage types). The voice processing engine 608 can identify the keywords using a data structure, such as a lookup table, that indicates keywords for the procedure. The voice processing engine 608 can evaluate the speech data 216 to periodically identify and/or update the procedure state, such as by evaluating each detected word, or a subset of detected words (e.g., according to a schedule of when to evaluate detected speech data 216 for keywords) to determine and/or update the procedure state.

The voice processing engine 608 can determine the speech data 216 using the procedure state. For example, the voice processing engine 608 can apply the procedure state as input to the speech model 636 (e.g., as the state; together with the audio data 212; together with the audio data 212 and the identifier of the procedure). In some implementations, the voice processing engine 608 determines the speech data 216 using the procedure state for at least one of (i) a predetermined duration subsequent to determining the procedure state or (ii) until an update of the procedure state as determined by the system 600. This can enable the voice processing engine 608 to use the procedure state to more accurately determine the speech data 216. In some implementations, the voice processing engine 608 determines a confidence score (e.g., confidence value, probability score) of each of a plurality of candidate speech data (e.g., candidate phrases 540) based on at least one of the state, the identifier of the procedure, or the procedure state, and determines the speech data 216 according to the respective confidence scores. For example, the voice processing engine 608 can select a candidate speech data of the plurality of candidate speech data having the highest confidence score as the detected speech data 216. For example, responsive to determining the procedure state to relate to the keyword "stenosis," the voice processing engine 608 can determine relatively higher confidence scores for candidate speech data relating to anatomical features having stenosis rather than candidate speech data relating to initial steps of the procedure (e.g., before any stenosis would be identified).

The voice processing engine 608 can assign the speech data 216 to the subject data record 606 based on at least one of the state (e.g., state of the subject) or the procedure state. For example, the voice processing engine 608 can identify, based on one or more keywords of the speech data 216, a corresponding field of the subject data record 606 to which to assign the speech data 216. The voice processing engine 608 can determine whether to assign the speech data 216 based on the training of the speech model 636 (e.g., based on training examples indicating examples of speech that is assigned to electronic records or is not assigned to electronic records).

Referring further to FIG. 6, the system 600 can use the voice processing engine 608 to determine, from the speech data 216, one or more findings. The system 600 can determine and/or update at least one of the state of the subject or the procedure state according to the determined findings. For example, as noted above, the system 600 can determine speech data 216 indicating characteristics of findings such as blood vessel, blockage type, and/or vessel structural relationships, such as "right coronary artery 40% stenosis;" "LAD is a moderate caliber vessel, first diagonal branch is 60% stenosis;" "the left circumflex is a moderate caliber vessel giving rise to two obtuse marginal branches and the left posterior descending artery, there is a 80% stenosis at the mid circumflex near where the second obtuse marginal branch takes off, the second obtuse marginal branch has a 70% stenosis;" "the RCA is a small caliber vessel giving rise to the right posterior descending artery;" "it is normal;" and "the left main is a large caliber vessel giving rise to the left anterior descending and left circumflex arteries, there is a patent stent in the left main." Various such speech data 216 may refer to features discussed in other speech data 216 (e.g., previously detected phrases 640 or other parts of speech); the voice processing engine 608 can use at least one of the state or the procedure state to more effectively detect speech 216 and relate the detected speech 216 to particular findings and/or fields of the subject data record 606. The system 600 can determine at least one of diagnosis data 618 or therapeutic data 619 from the speech data 216, including by matching keywords or according to training of the voice processing engine 608. The system 600 can assign speech data 216, based on at least one of the content of the speech data 216, the state, or the procedure state, to defined fields such as Left ventriculography and Hemodynamics; LVEDP; Estimated Ejection Fraction; Wall motion; Valve function; Coronary angiography; Dominance; or various other fields of cardiological data records.

In some implementations, the system 600 performs free form assignment of speech data 216. For example, the voice processing engine 608 can be configured to determine that particular speech data 216 satisfies a criteria for assignment to the subject data record 608, such as to a free form entry field of the subject data record 608 (e.g., responsive to determining that a more specific field of the subject data record 608 is not available for assigning the speech data 216). The speech data 216 can include, for example, recommendations, history, conclusions, procedure notes, equipment used, patient state, start time, and/or end time of the procedure.

Referring further to FIGS. 2 and 4-6, one or more aspects of the systems 200, 400, 500, and/or 600 may be implemented for various procedures that involve accurately detecting speech during the procedures and correctly recording the detected speech (and not recording noise) to subject data records. For example, the systems described herein may be implemented for various medical specialty procedures (e.g., domain-specific procedures) including but not limited to orthopedic, pulmonary/pulmonological, neurological, pediatric, and OB/GYN procedures. As described with reference to examples of the systems 200, 400, 500, and/or 600, systems in accordance with the present disclosure can include speech models that are trained using training data that includes domain-specific audio data from particular procedures, at least one of speech data determined (e.g., correctly determined) from the audio data or text data recorded to electronic records corresponding to the procedures, and at least one of state information or identifiers of the procedures being performed. The systems can determine, from the speech data, indications of directions or commands for navigating the electronic records in order to assign the speech data to appropriate fields of the electronic records. As such, the speech models and/or voice processing engines can be trained to detect speech with high accuracy, precision, and/or recall, and to effectively assign text corresponding to the detected speech to the electronic records (e.g., while not assigning text data corresponding to noise, such as conversational speech that may be occurring during the procedures that may not be pertinent for recording).

Figure 7A:
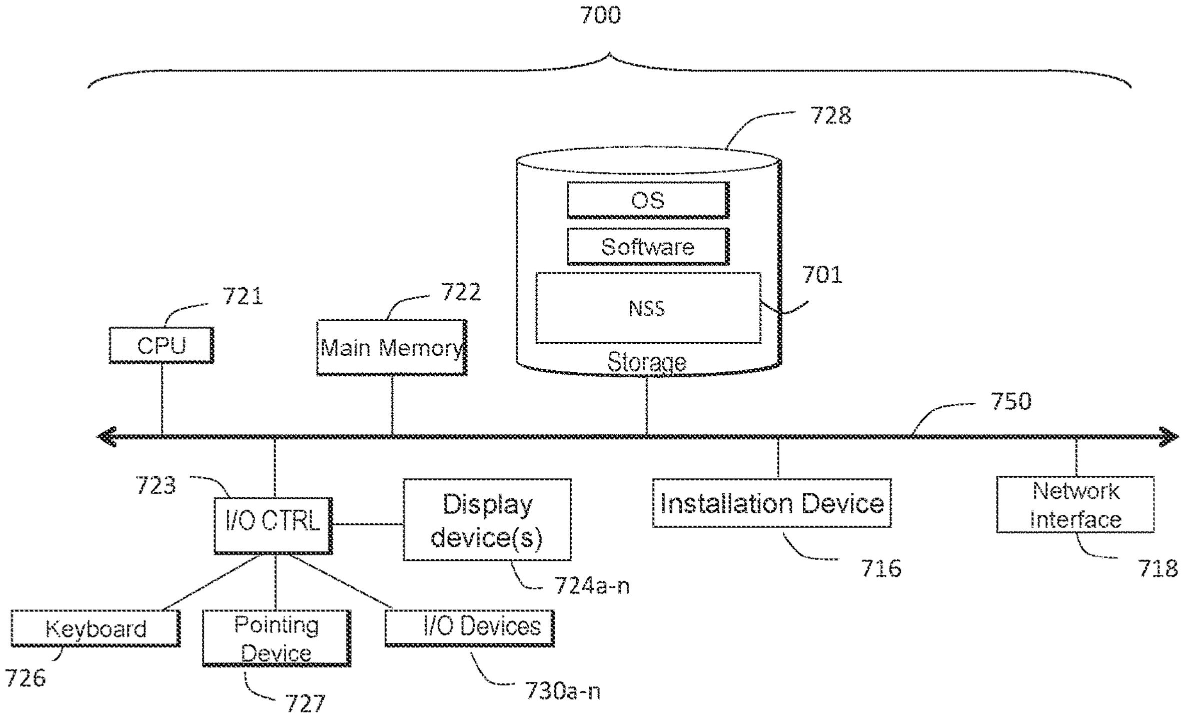
FIGS. 7A and 7B depict block diagrams of an example of a computing environment.
Figure 7B:
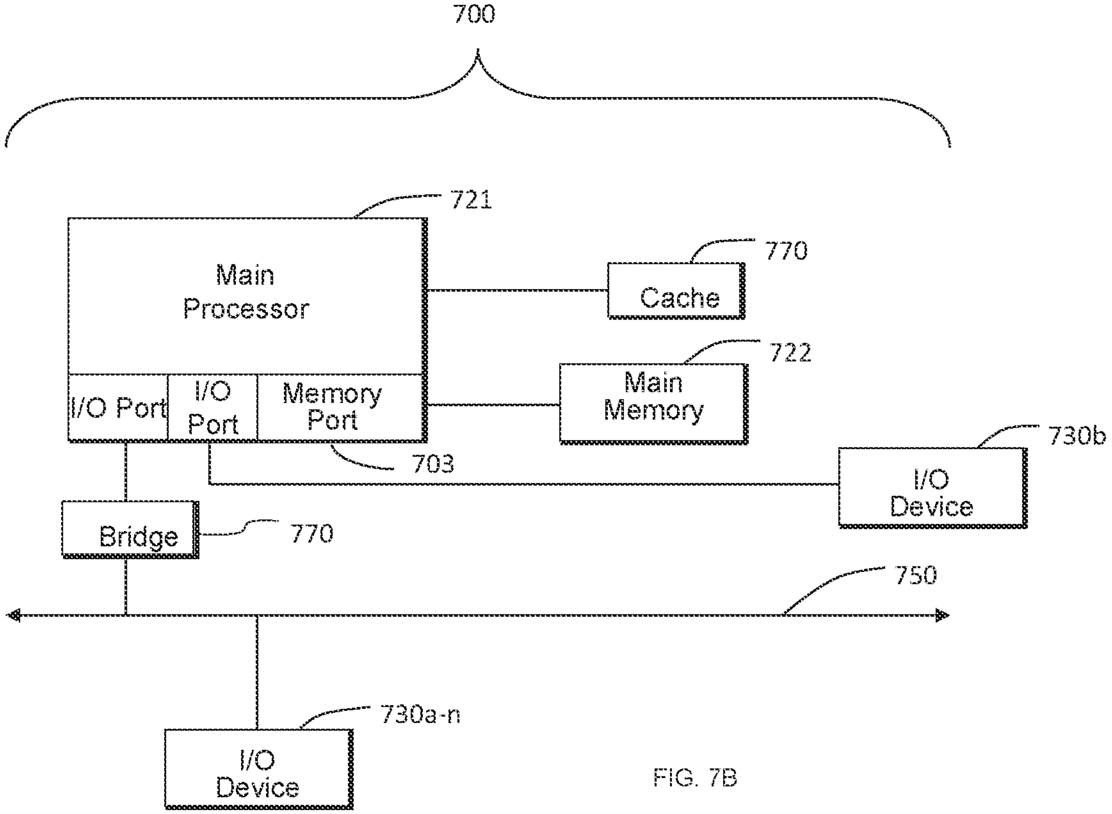

FIGS. 7A and 7B depict block diagrams of a computing device 700. As shown in FIGS. 7A and 7B, each computing device 700 includes a central processing unit 721, and a main memory unit 722. As shown in FIG. 7A, a computing device 700 can include a storage device 728, an installation device 716, a network interface 718, an I/O controller 723, display devices 724*a*-724*n*, a keyboard 726 and a pointing device 727, e.g. a mouse. The storage device 728 can include, without limitation, an operating system, software, and software of the systems 200, 400, 500, and/or 600. As shown in FIG. 7B, each computing device 700 can also include additional optional elements, e.g. a memory port 703, a bridge 770, one or more input/output devices 730*a*-730*n* (generally referred to using reference numeral 730), and a cache memory 740 in communication with the central processing unit 721.

The central processing unit 721 is any logic circuitry that responds to and processes instructions fetched from the main memory unit 722. In many embodiments, the central processing unit 721 is provided by a microprocessor unit, e.g.: those manufactured by Intel Corporation of Mountain View, California; those manufactured by Motorola Corporation of Schaumburg, Illinois; the ARM processor (from, e.g., ARM Holdings and manufactured by ST, TI, ATMEL, etc.) and TEGRA system on a chip (SoC) manufactured by Nvidia of Santa Clara, California; the POWER7 processor, those manufactured by International Business Machines of White Plains, New York; or those manufactured by Advanced Micro Devices of Sunnyvale, California; or field programmable gate arrays ("FPGAs") from Altera in San Jose, CA, Intel Corporation, Xlinix in San Jose, CA, or MicroSemi in Aliso Viejo, CA, etc. The computing device 700 can be based on any of these processors, or any other processor capable of operating as described herein. The central processing unit 721 can utilize instruction level parallelism, thread level parallelism, different levels of cache, and multi-core processors. A multi-core processor can include two or more processing units on a single computing component. Examples of multi-core processors include the AMD PHENOM IIX2, INTEL CORE i5 and INTEL CORE i7.

Main memory unit 722 can include one or more memory chips capable of storing data and allowing any storage location to be directly accessed by the microprocessor 721. Main memory unit 722 can be volatile and faster than storage 728 memory. Main memory units 722 can be Dynamic random access memory (DRAM) or any variants, including static random access memory (SRAM), Burst SRAM or SynchBurst SRAM (BSRAM), Fast Page Mode DRAM (FPM DRAM), Enhanced DRAM (EDRAM), Extended Data Output RAM (EDO RAM), Extended Data Output DRAM (EDO DRAM), Burst Extended Data Output DRAM (BEDO DRAM), Single Data Rate Synchronous DRAM (SDR SDRAM), Double Data Rate SDRAM (DDR SDRAM), Direct Rambus DRAM (DRDRAM), or Extreme Data Rate DRAM (XDR DRAM). In some embodiments, the main memory 722 or the storage 728 can be non-volatile; e.g., non-volatile read access memory (NVRAM), flash memory non-volatile static RAM (nvSRAM), Ferroelectric RAM (FeRAM), Magnetoresistive RAM (MRAM), Phase-change memory (PRAM), conductive-bridging RAM (CBRAM), Silicon-Oxide-Nitride-Oxide-Silicon (SONOS), Resistive RAM (RRAM), Racetrack, Nano-RAM (NRAM), or Millipede memory. The main memory 722 can be based on any of the above described memory chips, or any other available memory chips capable of operating as described herein. In the embodiment shown in FIG. 7A, the processor 721 communicates with main memory 722 via a system bus 750 (described in more detail below). FIG. 7B depicts an embodiment of a computing device 700 in which the processor communicates directly with main memory 722 via a memory port 703. For example, in FIG. 7B the main memory 722 can be DRDRAM.

FIG. 7B depicts an embodiment in which the main processor 721 communicates directly with cache memory 740 via a secondary bus, sometimes referred to as a backside bus. In other embodiments, the main processor 721 communicates with cache memory 740 using the system bus 750. Cache memory 740 typically has a faster response time than main memory 722 and is typically provided by SRAM, BSRAM, or EDRAM. In the embodiment shown in FIG. 7B, the processor 721 communicates with various I/O devices 730 via a local system bus 750. Various buses can be used to connect the central processing unit 721 to any of the I/O devices 730, including a PCI bus, a PCI-X bus, or a PCI-Express bus, or a NuBus. For embodiments in which the I/O device is a video display 724, the processor 721 can use an Advanced Graphics Port (AGP) to communicate with the display 724 or the I/O controller 723 for the display 724. FIG. 7B depicts an embodiment of a computer 700 in which the main processor 721 communicates directly with I/O device 730*b* or other processors 721' via HYPERTRANSPORT, RAPIDIO, or INFINIBAND communications technology. FIG. 7B also depicts an embodiment in which local busses and direct communication are mixed: the processor 721 communicates with I/O device 730*a* using a local interconnect bus while communicating with I/O device 730*b* directly.

A wide variety of I/O devices 730*a*-730*n* can be present in the computing device 700. Input devices can include keyboards, mice, trackpads, trackballs, touchpads, touch mice, multi-touch touchpads and touch mice, microphones (analog or MEMS), multi-array microphones, drawing tablets, cameras, single-lens reflex camera (SLR), digital SLR (DSLR), CMOS sensors, CCDs, accelerometers, inertial measurement units, infrared optical sensors, pressure sensors, magnetometer sensors, angular rate sensors, depth sensors, proximity sensors, ambient light sensors, gyroscopic sensors, or other sensors. Output devices can include video displays, graphical displays, speakers, headphones, inkjet printers, laser printers, and 3D printers.

Devices 730*a*-730*n* can include a combination of multiple input or output devices, including, e.g., Microsoft KINECT, Nintendo Wiimote for the WII, Nintendo WII U GAMEPAD, or Apple IPHONE. Some devices 730*a*-730*n* allow gesture recognition inputs through combining some of the inputs and outputs. Some devices 730*a*-730*n* provides for facial recognition which can be utilized as an input for different purposes including authentication and other commands. Some devices 730*a*-730*n* provides for voice recognition and inputs, including, e.g., Microsoft KINECT, SIRI for IPHONE by Apple, Google Now or Google Voice Search.

Additional devices 730*a*-730*n* have both input and output capabilities, including, e.g., haptic feedback devices, touchscreen displays, or multi-touch displays. Touchscreen, multi-touch displays, touchpads, touch mice, or other touch sensing devices can use different technologies to sense touch, including, e.g., capacitive, surface capacitive, projected capacitive touch (PCT), in-cell capacitive, resistive, infrared, waveguide, dispersive signal touch (DST), in-cell optical, surface acoustic wave (SAW), bending wave touch (BWT), or force-based sensing technologies. Some multi-touch devices can allow two or more contact points with the surface, allowing advanced functionality including, e.g., pinch, spread, rotate, scroll, or other gestures. Some touchscreen devices, including, e.g., Microsoft PIXELSENSE or Multi-Touch Collaboration Wall, can have larger surfaces, such as on a table-top or on a wall, and can also interact with other electronic devices. Some I/O devices 730*a*-730*n*, display devices 724*a*-724*n* or group of devices can be augmented reality devices. The I/O devices can be controlled by an I/O controller 721 as shown in FIG. 7A. The I/O controller 721 can control one or more I/O devices, such as, e.g., a keyboard 126 and a pointing device 727, e.g., a mouse or optical pen. Furthermore, an I/O device can also provide storage and/or an installation medium 116 for the computing device 700. In still other embodiments, the computing device 700 can provide USB connections (not shown) to receive handheld USB storage devices. In further embodiments, an I/O device 730 can be a bridge between the system bus 750 and an external communication bus, e.g. a USB bus, a SCSI bus, a FireWire bus, an Ethernet bus, a Gigabit Ethernet bus, a Fibre Channel bus, or a Thunderbolt bus.

In some embodiments, display devices 724*a*-724*n* can be connected to I/O controller 721. Display devices can include, e.g., liquid crystal displays (LCD), thin film transistor LCD (TFT-LCD), blue phase LCD, electronic papers (e-ink) displays, flexile displays, light emitting diode displays (LED), digital light processing (DLP) displays, liquid crystal on silicon (LCOS) displays, organic light-emitting diode (OLED) displays, active-matrix organic light-emitting diode (AMOLED) displays, liquid crystal laser displays, time-multiplexed optical shutter (TMOS) displays, or 3D displays. Examples of 3D displays can use, e.g. stereoscopy, polarization filters, active shutters, or autostereoscopy. Display devices 724*a*-724*n* can also be a head-mounted display (HMD). In some embodiments, display devices 724*a*-724*n* or the corresponding I/O controllers 723 can be controlled through or have hardware support for OPENGL or DIRECTX API or other graphics libraries.

In some embodiments, the computing device 700 can include or connect to multiple display devices 724*a*-724*n*, which each can be of the same or different type and/or form. As such, any of the I/O devices 730*a*-730*n* and/or the I/O controller 723 can include any type and/or form of suitable hardware, software, or combination of hardware and software to support, enable or provide for the connection and use of multiple display devices 724*a*-724*n* by the computing device 700. For example, the computing device 700 can include any type and/or form of video adapter, video card, driver, and/or library to interface, communicate, connect or otherwise use the display devices 724*a*-724*n*. In one embodiment, a video adapter can include multiple connectors to interface to multiple display devices 724*a*-724*n*. In other embodiments, the computing device 700 can include multiple video adapters, with each video adapter connected to one or more of the display devices 724*a*-724*n*. In some embodiments, any portion of the operating system of the computing device 700 can be configured for using multiple displays 724*a*-724*n*. In other embodiments, one or more of the display devices 724*a*-724*n* can be provided by one or more other computing devices 700*a* or 700*b* connected to the computing device 700, via the network 740. In some embodiments software can be designed and constructed to use another computer's display device as a second display device 724*a* for the computing device 700. For example, in one embodiment, an Apple iPad can connect to a computing device 700 and use the display of the device 700 as an additional display screen that can be used as an extended desktop. One ordinarily skilled in the art will recognize and appreciate the various ways and embodiments that a computing device 700 can be configured to have multiple display devices 724*a*-724*n*.

Referring again to FIG. 7A, the computing device 700 can comprise a storage device 728 (e.g. one or more hard disk drives or redundant arrays of independent disks) for storing an operating system or other related software, and for storing application software programs such as any program related to the software for the system 200. Examples of storage device 728 include, e.g., hard disk drive (HDD); optical drive including CD drive, DVD drive, or BLU-RAY drive; solid-state drive (SSD); USB flash drive; or any other device suitable for storing data. Some storage devices can include multiple volatile and non-volatile memories, including, e.g., solid state hybrid drives that combine hard disks with solid state cache. Some storage device 728 can be non-volatile, mutable, or read-only. Some storage device 728 can be internal and connect to the computing device 700 via a bus 750. Some storage device 728 can be external and connect to the computing device 700 via a I/O device 730 that provides an external bus. Some storage device 728 can connect to the computing device 700 via the network interface 718 over a network, including, e.g., the Remote Disk for MACBOOK AIR by Apple. Some client devices 700 can not require a non-volatile storage device 728 and can be thin clients or zero clients 202. Some storage device 728 can also be used as an installation device 716, and can be suitable for installing software and programs. Additionally, the operating system and the software can be run from a bootable medium, for example, a bootable CD, e.g. KNOPPIX, a bootable CD for GNU/Linux that is available as a GNU/Linux distribution from knoppix.net.

Computing device 700 can also install software or application from an application distribution platform. Examples of application distribution platforms include the App Store for iOS provided by Apple, Inc., the Mac App Store provided by Apple, Inc., GOOGLE PLAY for Android OS provided by Google Inc., Chrome Webstore for CHROME OS provided by Google Inc., and Amazon Appstore for Android OS and KINDLE FIRE provided by Amazon.com, Inc. Computing device 700 install software or applications from a source (e.g., server) maintained by a proprietor of the software or applications, such as a source independent of an application distribution platform.

Furthermore, the computing device 700 can include a network interface 718 to interface to the network 740 through a variety of connections including, but not limited to, standard telephone lines LAN or WAN links (e.g., 802.11, T1, T3, Gigabit Ethernet, Infiniband), broadband connections (e.g., ISDN, Frame Relay, ATM, Gigabit Ethernet, Ethernet-over-SONET, ADSL, VDSL, BPON, GPON, fiber optical including FiOS), wireless connections, or some combination of any or all of the above. Connections can be established using a variety of communication protocols (e.g., TCP/IP, Ethernet, ARCNET, SONET, SDH, Fiber Distributed Data Interface (FDDI), IEEE 802.11a/b/g/n/ac CDMA, GSM, WiMax and direct asynchronous connections). In one embodiment, the computing device 700 communicates with other computing devices 700' via any type and/or form of gateway or tunneling protocol e.g. Secure Socket Layer (SSL) or Transport Layer Security (TLS), or the Citrix Gateway Protocol manufactured by Citrix Systems, Inc. of Ft. Lauderdale, Florida. The network interface 118 can comprise a built-in network adapter, network interface card, PCMCIA network card, EXPRESSCARD network card, card bus network adapter, wireless network adapter, USB network adapter, modem or any other device suitable for interfacing the computing device 700 to any type of network capable of communication and performing the operations described herein.

A computing device 700 of the sort depicted in FIG. 7A can operate under the control of an operating system, which controls scheduling of tasks and access to system resources. The computing device 700 can be running any operating system such as any of the versions of the MICROSOFT WINDOWS operating systems, the different releases of the Unix and Linux operating systems, any version of the MAC OS for Macintosh computers, any embedded operating system, any real-time operating system, any open source operating system, any proprietary operating system, any operating systems for mobile computing devices, or any other operating system capable of running on the computing device and performing the operations described herein. Typical operating systems include, but are not limited to: WINDOWS 7000, WINDOWS Server 2012, WINDOWS CE, WINDOWS Phone, WINDOWS XP, WINDOWS VISTA, and WINDOWS 7, WINDOWS RT, and WINDOWS 8 all of which are manufactured by Microsoft Corporation of Redmond, Washington; MAC OS and iOS, manufactured by Apple, Inc. of Cupertino, California; and Linux, a freely-available operating system, e.g. Linux Mint distribution ("distro") or Ubuntu, distributed by Canonical Ltd. of London, United Kingdom; or Unix or other Unix-like derivative operating systems; and Android, designed by Google, of Mountain View, California, among others. Some operating systems, including, e.g., the CHROME OS by Google, can be used on zero clients or thin clients, including, e.g., CHROMEBOOKS.

The computer system 700 can be any workstation, telephone, desktop computer, laptop or notebook computer, netbook, ULTRABOOK, tablet, server, handheld computer, mobile telephone, smartphone or other portable telecommunications device, media playing device, a gaming system, mobile computing device, or any other type and/or form of computing, telecommunications or media device that is capable of communication. The computer system 700 has sufficient processor power and memory capacity to perform the operations described herein. In some embodiments, the computing device 700 can have different processors, operating systems, and input devices consistent with the device. The Samsung GALAXY smartphones, e.g., operate under the control of Android operating system developed by Google, Inc. GALAXY smartphones receive input via a touch interface.

In some embodiments, the computing device 700 is a gaming system. For example, the computer system 700 can comprise a PLAYSTATION 3, or PERSONAL PLAYSTATION PORTABLE (PSP), or a PLAYSTATION VITA device manufactured by the Sony Corporation of Tokyo, Japan, a NINTENDO DS, NINTENDO 3DS, NINTENDO WII, or a NINTENDO WII U device manufactured by Nintendo Co., Ltd., of Kyoto, Japan, or an XBOX 360 device manufactured by the Microsoft Corporation of Redmond, Washington, or an OCULUS RIFT or OCULUS VR device manufactured BY OCULUS VR, LLC of Menlo Park, California.

In some embodiments, the computing device 700 is a digital audio player such as the Apple IPOD, IPOD Touch, and IPOD NANO lines of devices, manufactured by Apple Computer of Cupertino, California. Some digital audio players can have other functionality, including, e.g., a gaming system or any functionality made available by an application from a digital application distribution platform. For example, the IPOD Touch can access the Apple App Store. In some embodiments, the computing device 700 is a portable media player or digital audio player supporting file formats including, but not limited to, MP3, WAV, M4A/AAC, WMA Protected AAC, AIFF, Audible audiobook, Apple Lossless audio file formats and .mov, .m4v, and .mp4 MPEG-4 (H.264/MPEG-4 AVC) video file formats.

In some embodiments, the computing device 700 is a tablet e.g. the IPAD line of devices by Apple; GALAXY TAB family of devices by Samsung; or KINDLE FIRE, by Amazon.com, Inc. of Seattle, Washington. In other embodiments, the computing device 700 is an eBook reader, e.g. the KINDLE family of devices by Amazon.com, or NOOK family of devices by Barnes & Noble, Inc. of New York City, New York.

In some embodiments, the communications device 700 includes a combination of devices, e.g. a smartphone combined with a digital audio player or portable media player. For example, one of these embodiments is a smartphone, e.g. the IPHONE family of smartphones manufactured by Apple, Inc.; a Samsung GALAXY family of smartphones manufactured by Samsung, Inc.; or a Motorola DROID family of smartphones. In yet another embodiment, the communications device 700 is a laptop or desktop computer equipped with a web browser and a microphone and speaker system, e.g. a telephony headset. In these embodiments, the communications devices 700 are web-enabled and can receive and initiate phone calls. In some embodiments, a laptop or desktop computer is also equipped with a webcam or other video capture device that enables video chat and video call.

In some embodiments, the status of one or more machines 700 in the network are monitored, generally as part of network management. In one of these embodiments, the status of a machine can include an identification of load information (e.g., the number of processes on the machine, CPU and memory utilization), of port information (e.g., the number of available communication ports and the port addresses), or of session status (e.g., the duration and type of processes, and whether a process is active or idle). In another of these embodiments, this information can be identified by a plurality of metrics, and the plurality of metrics can be applied at least in part towards decisions in load distribution, network traffic management, and network failure recovery as well as any aspects of operations of the present solution described herein. Aspects of the operating environments and components described above will become apparent in the context of the systems and methods disclosed herein.

All or part of the processes described herein and their various modifications (hereinafter referred to as "the processes") can be implemented, at least in part, via a computer program product, i.e., a computer program tangibly embodied in one or more tangible, physical hardware storage devices that are computer and/or machine-readable storage devices for execution by, or to control the operation of, data processing apparatus, e.g., a programmable processor, a computer, or multiple computers. A computer program can be written in any form of programming language, including compiled or interpreted languages, and it can be deployed in any form, including as a stand-alone program or as a module, component, subroutine, or other unit suitable for use in a computing environment. A computer program can be deployed to be executed on one computer or on multiple computers at one site or distributed across multiple sites and interconnected by a network.

Processors suitable for the execution of a computer program include, by way of example, both general and special purpose microprocessors, and any one or more processors of any kind of digital computer. Generally, a processor will receive instructions and data from a read-only storage area or a random access storage area or both. Elements of a computer (including a server) include one or more processors for executing instructions and one or more storage area devices for storing instructions and data. Generally, a computer will also include, or be operatively coupled to receive data from, or transfer data to, or both, one or more machine-readable storage media, such as mass storage devices for storing data, e.g., magnetic, magneto-optical disks, or optical disks.

Computer program products are stored in a tangible form on non-transitory computer readable media and non-transitory physical hardware storage devices that are suitable for embodying computer program instructions and data. These include all forms of non-volatile storage, including by way of example, semiconductor storage area devices, e.g., EPROM, EEPROM, and flash storage area devices; magnetic disks, e.g., internal hard disks or removable disks; magneto-optical disks; and CD-ROM and DVD-ROM disks and volatile computer memory, e.g., RAM such as static and dynamic RAM, as well as erasable memory, e.g., flash memory and other non-transitory devices.

The construction and arrangement of the systems and methods as shown in the various embodiments are illustrative only. Although only a few embodiments have been described in detail in this disclosure, many modifications are possible (e.g., variations in sizes, dimensions, structures, shapes and proportions of the various elements, values of parameters, mounting arrangements, use of materials, colors, orientations, etc.). For example, the position of elements may be reversed or otherwise varied and the nature or number of discrete elements or positions may be altered or varied. Accordingly, all such modifications are intended to be included within the scope of the present disclosure. The order or sequence of any process or method steps may be varied or re-sequenced. Other substitutions, modifications, changes, and omissions may be made in the design, operating conditions and arrangement of embodiments without departing from the scope of the present disclosure.

As utilized herein, the terms "approximately," "about," "substantially", and similar terms are intended to include any given ranges or numbers +/−10%. These terms include insubstantial or inconsequential modifications or alterations of the subject matter described and claimed are considered to be within the scope of the disclosure as recited in the appended claims.

It should be noted that the term "exemplary" and variations thereof, as used herein to describe various embodiments, are intended to indicate that such embodiments are possible examples, representations, or illustrations of possible embodiments (and such terms are not intended to connote that such embodiments are necessarily extraordinary or superlative examples).

The term "coupled" and variations thereof, as used herein, means the joining of two members directly or indirectly to one another. Such joining may be stationary (e.g., permanent or fixed) or moveable (e.g., removable or releasable). Such joining may be achieved with the two members coupled directly to each other, with the two members coupled to each other using a separate intervening member and any additional intermediate members coupled with one another, or with the two members coupled to each other using an intervening member that is integrally formed as a single unitary body with one of the two members. If "coupled" or variations thereof are modified by an additional term (e.g., directly coupled), the generic definition of "coupled" provided above is modified by the plain language meaning of the additional term (e.g., "directly coupled" means the joining of two members without any separate intervening member), resulting in a narrower definition than the generic definition of "coupled" provided above. Such coupling may be mechanical, electrical, or fluidic.

The term "or," as used herein, is used in its inclusive sense (and not in its exclusive sense) so that when used to connect a list of elements, the term "or" means one, some, or all of the elements in the list. Conjunctive language such as the phrase "at least one of X, Y, and Z," unless specifically stated otherwise, is understood to convey that an element may be either X, Y, Z; X and Y; X and Z; Y and Z; or X, Y, and Z (i.e., any combination of X, Y, and Z). Thus, such conjunctive language is not generally intended to imply that certain embodiments require at least one of X, at least one of Y, and at least one of Z to each be present, unless otherwise indicated.

References herein to the positions of elements (e.g., "top," "bottom," "above," "below") are merely used to describe the orientation of various elements in the FIGURES. It should be noted that the orientation of various elements may differ according to other exemplary embodiments, and that such variations are intended to be encompassed by the present disclosure.

The present disclosure contemplates methods, systems and program products on any machine-readable media for accomplishing various operations. The embodiments of the present disclosure may be implemented using existing computer processors, or by a special purpose computer processor for an appropriate system, incorporated for this or another purpose, or by a hardwired system. Embodiments within the scope of the present disclosure include program products comprising machine-readable media for carrying or having machine-executable instructions or data structures stored thereon. Such machine-readable media can be any available media that can be accessed by a general purpose or special purpose computer or other machine with a processor. By way of example, such machine-readable media can comprise RAM, ROM, EPROM, EEPROM, CD-ROM or other optical disk storage, magnetic disk storage or other magnetic storage devices, or any other medium which can be used to carry or store desired program code in the form of machine-executable instructions or data structures and which can be accessed by a general purpose or special purpose computer or other machine with a processor. Combinations of the above are also included within the scope of machine-readable media. Machine-executable instructions include, for example, instructions and data which cause a general purpose computer, special purpose computer, or special purpose processing machines to perform a certain function or group of functions.

Although the figures show a specific order of method steps, the order of the steps may differ from what is depicted. Also two or more steps may be performed concurrently or with partial concurrence. Such variation will depend on the software and hardware systems chosen and on designer choice. All such variations are within the scope of the disclosure. Likewise, software implementations could be accomplished with standard programming techniques with rule based logic and other logic to accomplish the various connection steps, processing steps, comparison steps and decision steps.

What is claimed is:

1. A method of operating a voice assistant, comprising:

detecting, by one or more processors, a domain of a procedure being performed on a subject;

receiving, by the one or more processors, audio data during the procedure;

detecting, by the one or more processors, a state of an electronic record associated with the subject, the state comprising a current location of the electronic record identifying at least one field for data entry corresponding to the procedure;

applying, by the one or more processors, the domain, the state, and the audio data as input to at least one machine learning model to cause the at least one machine learning model to generate speech data representative of the audio data that comprises (1) a command for navigation of the electronic record and (2) a value for entry in the electronic record, the at least one machine learning model configured using example data relating to the domain;

selecting, by the one or more processors, a field of the electronic record based at least on the state and the command, the field corresponding to the procedure; and assigning, by the one or more processors, the value to the field.

2. The method of claim 1, wherein detecting the domain comprises:

identifying, by the one or more processors, an identifier of at least one of the electronic record or the subject; and selecting, by the one or more processors, the domain based at least on the identifier.

3. The method of claim 1, wherein the state comprises a location in the electronic record, the method further comprising applying the state as input to the at least one speech model to cause the at least one speech model to generate the speech data.

4. The method of claim 1, wherein the at least one speech model comprises one or more neural networks.

5. The method of claim 1, wherein the audio data comprises a duration of audio of at least five seconds.

6. The method of claim 1, wherein the at least one speech model is configured using training data that includes at least one of noise or a speed change.

7. The method of claim 1, wherein the at least one speech model is configured training data that includes a first subset of training data having context information corresponding to the domain and a second subset of training data not having context information.

8. The method of claim 1, wherein the domain comprises at least one of a dental, restorative, surgical, medical, cardiological, or gastrointestinal domain.

9. The method of claim 1, wherein selecting the field of the electronic record comprising generating one or more HTML commands corresponding to the command to navigate to the field, the one or more HTML commands representative of at least one of a keystroke or a mouseclick to apply to an interface of a client device on which the electronic record is accessible.

10. The method of claim 1, wherein assigning the value to the field comprises generating one or more HTML commands corresponding to the value and representative of at least one of a keystroke or a mouseclick to apply to an interface of a client device on which the electronic record is accessible.

11. The method of claim 1, wherein applying the domain as input to the at least one machine learning model causes the at least one machine learning model to promote confidence values for domain-specific terminology in the audio data.

12. The method of claim 1, wherein the at least one machine learning model is configured to determine whether to classify the speech data represented by the audio data, based at least on the domain of the procedure, into a class for assignment to the electronic record.

13. A system, comprising:

one or more processors to:

detect a domain of a procedure being performed on a subject;

receive audio data during the procedure;

detect a state of an electronic record associated with the subject, the state comprising a current location of the electronic record identifying at least one field for data entry corresponding to the procedure;

apply the domain, the state, and the audio data as input to at least one machine learning model to cause the at least one machine learning model to generate speech data representative of the audio data that comprises (1) a command for navigation of the electronic record and (2) a value for entry in the electronic record, the at least one machine learning model configured using example data relating to the domain;

select a field of the electronic record based at least on the state and the command, the field corresponding to the procedure; and assign the value to the field.

14. The system of claim 13, wherein the one or more processors are to detect the domain by:

identifying an identifier of at least one of the electronic record or the subject; and selecting the domain based at least on the identifier.

15. The system of claim 13, wherein the state comprises a location in the electronic record, and the one or more processors are to apply the state as input to the at least one speech model to cause the at least one speech model to generate the speech data.

16. The system of claim 13, wherein the at least one speech model comprises one or more neural networks.

17. The system of claim 13, wherein the audio data comprises a duration of audio of at least five seconds.

18. The system of claim 13, wherein the at least one speech model is configured using training data that includes at least one of noise or a speed change.

19. The system of claim 13, wherein the at least one speech model is configured training data that includes a first subset of training data having context information corresponding to the domain and a second subset of training data not having context information.

20. The system of claim 13, wherein the domain comprises at least one of a dental, restorative, surgical, medical, cardiological, or gastrointestinal domain.

* * * * *